(12) United States Patent
Sadeghi et al.

(10) Patent No.: US 11,779,665 B2
(45) Date of Patent: Oct. 10, 2023

(54) ELECTROCHEMICAL FLASH FLUORINATION AND RADIOFLUORINATION

(71) Applicant: The Regents of the University of California, Oakland, CA (US)

(72) Inventors: Saman Sadeghi, Los Angeles, CA (US); Mehrdad Balandeh, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/963,463

(22) PCT Filed: Feb. 4, 2019

(86) PCT No.: PCT/US2019/016561
§ 371 (c)(1),
(2) Date: Jul. 20, 2020

(87) PCT Pub. No.: WO2019/152958
PCT Pub. Date: Aug. 8, 2019

(65) Prior Publication Data
US 2020/0360541 A1    Nov. 19, 2020

Related U.S. Application Data

(60) Provisional application No. 62/625,817, filed on Feb. 2, 2018.

(51) Int. Cl.
| | |
|---|---|
| *A61K 51/04* | (2006.01) |
| *C07B 59/00* | (2006.01) |
| *C25B 3/23* | (2021.01) |
| *C25B 9/23* | (2021.01) |

(52) U.S. Cl.
CPC ............ *A61K 51/04* (2013.01); *C07B 59/001* (2013.01); *C25B 3/23* (2021.01); *C25B 9/23* (2021.01)

(58) Field of Classification Search
CPC .......... A61K 51/04; C07B 59/001; C25B 3/23
USPC ....................................................... 424/1.89
See application file for complete search history.

(56) References Cited

U.S. PATENT DOCUMENTS

| | | |
|---|---|---|
| 4,968,393 A | 11/1990 | Mazur et al. |
| 2009/0286992 A1 | 11/2009 | Carroll et al. |
| 2016/0137567 A1 | 5/2016 | Sadeghi et al. |

FOREIGN PATENT DOCUMENTS

WO    WO-2014183130 A1 * 11/2014 ............. A61K 51/04

OTHER PUBLICATIONS

Yoshida et al. Chem. Rev. 2018, 118, 4702-4730. (Year: 2018).*
Jorissen Electrochim. Acta 1996, 41, 553-562. (Year: 1996).*
Lebedev et al. PLoS One 2017, 1-19 (Year: 2017).*
Balandeh, M. et al. (2017, e-published Jul. 14, 2017). "Electrochemical Fluorination and Radiofluorination of Methyl(phenylthio)acetate Using Tetrabutylammonium Fluoride (TBAF)," J Electrochem Soc 164(9):G99-G103.
Balandeh, M. et al. (Nov. 13, 2018, e-published Aug. 30, 2018). "Electrochemical Flash Fluorination and Radiofluorination," ChemElectroChem 5(22):3353-3356.
Fuchigami, T. et al. (Oct. 2011, e-published Jun. 25, 2011). Selective electrochemical fluorination of organic molecules and macromolecules in ionic liquids, Chem Commun 47(37):10211-10223.
Fujie, S. et al. (Nov. 21, 2009). Thiofluorination of Carbon-Carbon Multiple Bonds Using Electrochemically Generated ArS (ARSSAr)$^+$ BF$_4^-$. Chemistry Letters 38(12):1186-1187.
He, Q. et al. (Sep. 2014, e-published Jun. 23, 2014). "Electrochemical nucleophilic synthesis of di-tert-butyl-(4-[18F]fluoro-1,2-phenylene)-dicarbonate," Appl Radiat Isot 92:52-57.
International Search Report dated Apr. 1, 2019 for PCT Application No. PCT/US2019/016561, filed Feb. 4, 2019, 4 pages.
Reischl, G. et al. (2002). "Electrochemical radiofluorination: Labeling of benzene with [18F]fluoride by nucleophilic substitution," Journal of Radioanalytical and Nuclear Chemistry 254(2):409-411.
Written Opinion dated Apr. 1, 2019 for PCT Application No. PCT/US2019/016561, filed Feb. 4, 2019, 10 pages.

* cited by examiner

*Primary Examiner* — Michael G. Hartley
*Assistant Examiner* — Sean R Donohue
(74) *Attorney, Agent, or Firm* — Mintz Levin Cohn Ferris Glovsky and Popeo, P.C.

(57) ABSTRACT

Provided herein are methods of fluorinating organic compounds. The electrochemical fluorination and radiofluorination of organic molecules using the cation pool technique is described, where the 18F and/or 19F-fluorine ions are added after the process of electrochemical oxidation, i.e., after formation of a carbocationic organic compound (i.e., a compound having a carbon atom with a positive charge).

11 Claims, 10 Drawing Sheets

ELECTROCHEMICAL FLASH FLUORINATION AND RADIOFLUORINATION

CROSS-REFERENCE TO RELATED APPLICATIONS

This application is a Section 371 US national phase of International Application No. PCT/US2019/016561 filed Feb. 4, 2019, which claims priority to U.S. Application No. 62/625,817 filed Feb. 2, 2018, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under Grant Number CA186842 awarded by the National Institutes of Health. The government has certain rights in the invention.

BACKGROUND

Fluorinated organic compounds have distinguishing physical, biological and chemical properties with a wide range of applications in fields such as agrochemicals, pharmaceuticals and materials science (O'Hagan et al, J. Fluor. Chem., 2010, 131, 1071-1081; Purser et al, Chem Soc Rev, 2008, 37, 320-330; Yamazaki et al, Fluorine in Medicinal Chemistry and Chemical Biology, ed. I. Ojima, John Wiley). Recently, there has been growing interest in the chemistry and properties of fluorinated organic compounds (Bgu et al, Bioorganic and Medicinal Chemistry of Fluorine, John Wiley & Sons, Inc., Hoboken, N.J.; Gillis et al, J. Med. Chem., 2015, 58, 8315-8359; Uneyama, Ed., in Organofluorine Chemistry, Blackwell Publishing, Oxford, UK, 2007, pp. 206-222). Fluorine gas and anhydrous HF have been broadly used for fluorination of organic compounds (Villalba et al, J. Ind. Ecol., 2008, 11, 85-101; Chambers et al, Chem. Commun., 2000, 959-960; Rozen, Acc. Chem. Res., 1996, 29, 243-248). However, these chemicals are costly, highly reactive, corrosive, hazardous, and therefore very difficult to handle.

Given the wide-ranging applications of fluorine in design of bioactive molecules and molecular imaging through positron emission tomography (PET), there is still a strong demand for further development of new synthetic methodologies to expand the chemist's toolbox for easier access to a broader scope of fluorinated and radiochemical compounds (Campbell et al, Nat. Chem., 2016, 9, 1-3). There have been significant recent developments in the area of nucleophilic fluorination and their application to radiochemistry with 18F-fluoride, such as synthesis of aryl fluorides directly from the corresponding phenols (Tang et al, J. Am. Chem. Soc., 2011, 133, 11482-11484), hypervalent iodine reagents used as fluorine sources in fluorocyclization reactions (Kohlhepp et al, Chem. Soc. Rev., 2016, 45, 6270-6288; Rotstein et al, Nat. Commun., 2014, 5, 4365), radiofluorination of diaryl-iodonium salts and Cu catalyzed mesityl-aryl-iodonium precursors (Ichiishi et al, Org. Lett., 2014, 16, 3224-3227), metal catalyzed aryl fluoride bond formation (Furuya et al, Nature, 2011, 473, 470), and recent reviews on these advances and their limitations (Preshlock et al, Chem. Rev., 2016, 116, 719-766).

Despite the development of modern fluorination techniques, many challenges still exist in terms of limited substrate scope, lack of functional group tolerance, difficulty in synthesizing the precursors and their stability, and the need for strict control of synthesis conditions. No one technique can address all the challenges for site specific fluorination. The electrochemical approach to fluorination stabilized cations presented herein provides a unique method for direct and very rapid fluorination in one step under mild conditions. The described method can target moieties such as thioethers not amenable to late-stage fluorination with existing methodologies, allowing their radiofluorination for PET tracer development.

There are provided herein inter alia solutions to these and other problems in the art.

BRIEF SUMMARY

Electrochemical fluorination of organic compounds can be a powerful alternative technique for direct fluorination. Electrochemical oxidation can create an electron-poor carbon, potentially without the need for chemical modification, preparing the organic molecules for nucleophilic fluorination. Fuchigami and S. Inagi, Chem. Commun., 2011, 47, 10211-23; Sawamura, K. Takahashi, S. Inagi and T. Fuchigami, Angew. Chem. Int. Ed., 2012, 51, 4413-4416. Fluorine atoms can be added to organic compounds in one step under mild conditions using electrochemistry, even for electron rich moieties such as aromatic and heteroaromatic rings, without the need to have leaving groups. Lebedev et al, PLOS ONE, 2017, 12, e0176606; He et al, Appl. Radiat. Isot., 2014, 92, 52-57.

Traditionally, the oxidative formation of a carbocation intermediate in electroorganic synthesis has been performed in the presence of an excess of nucleophile due to the instability of the carbocations. The presence of reactive and low oxidation potential nucleophiles and products in the anodic chamber during electrolysis can limit reaction yields and scope. To overcome this problem Yoshida (J. Am. Chem. Soc., 1999, 121, 9546-9549) developed the cation pool method, with which they could stabilize the carbocations formed during the electrochemical oxidation of carbamates by performing the electrochemical oxidation at low temperatures (negative 72° C.) followed by addition of nucleophiles such as allylsilanes post electrolysis. Subsequently, the same group reported thiofluorination of alkenes and alkynes using low-temperature anodic oxidation of ArSSAr in Bu4NBF4/$CH_2Cl_2$. Fujie et al, Chem. Lett., 2009, 38, 1186-1187. In their process, the counter anion of the supporting electrolyte (BF4−), which was present during the electrolysis, was also the source of fluoride.

Here, for the first time, the electrochemical fluorination and radiofluorination of organic molecules using the cation pool technique is described, where the $^{18}F$ and/or $^{19}F$-fluorine ions are added after the process of electrochemical oxidation, i.e., after formation of a carbocationic organic compound (i.e., a compound having a carbon atom with a positive charge). This approach enables the use of the cation pool method for the widely useful application of rapid and late-stage fluorination and radiochemistry.

BRIEF DESCRIPTION OF THE DRAWINGS

FIG. 7A shows the fluoride NMR of the product 2 for further identification of the fluorinated product obtained by cation pool method. The $^{19}$F-NMR was performed on the HPLC purified sample. FIG. 7B shows the fluoride NMR of the HPLC purified product 2 plus trifluoroacetic acid as standard.

Electrolysis was performed for 60 min at 1.6 V vs Ag wire at −20° C. using TFE solution containing 24 mM of 1, 142 mM of triflic acid. 2 ml of TFE solution containing 25 mM TBAP (also known as tetrabutylammonium perchlorate) and 5 mCi $^{18}$F-fluoride was added after electrolysis was finished and the sample was taken for analysis 30 min after 18F-fluoride addition. FIG. 8A shows UV HPLC and FIG. 8B shows gamma HPLC.

DETAILED DESCRIPTION

Definitions

Figure 1:
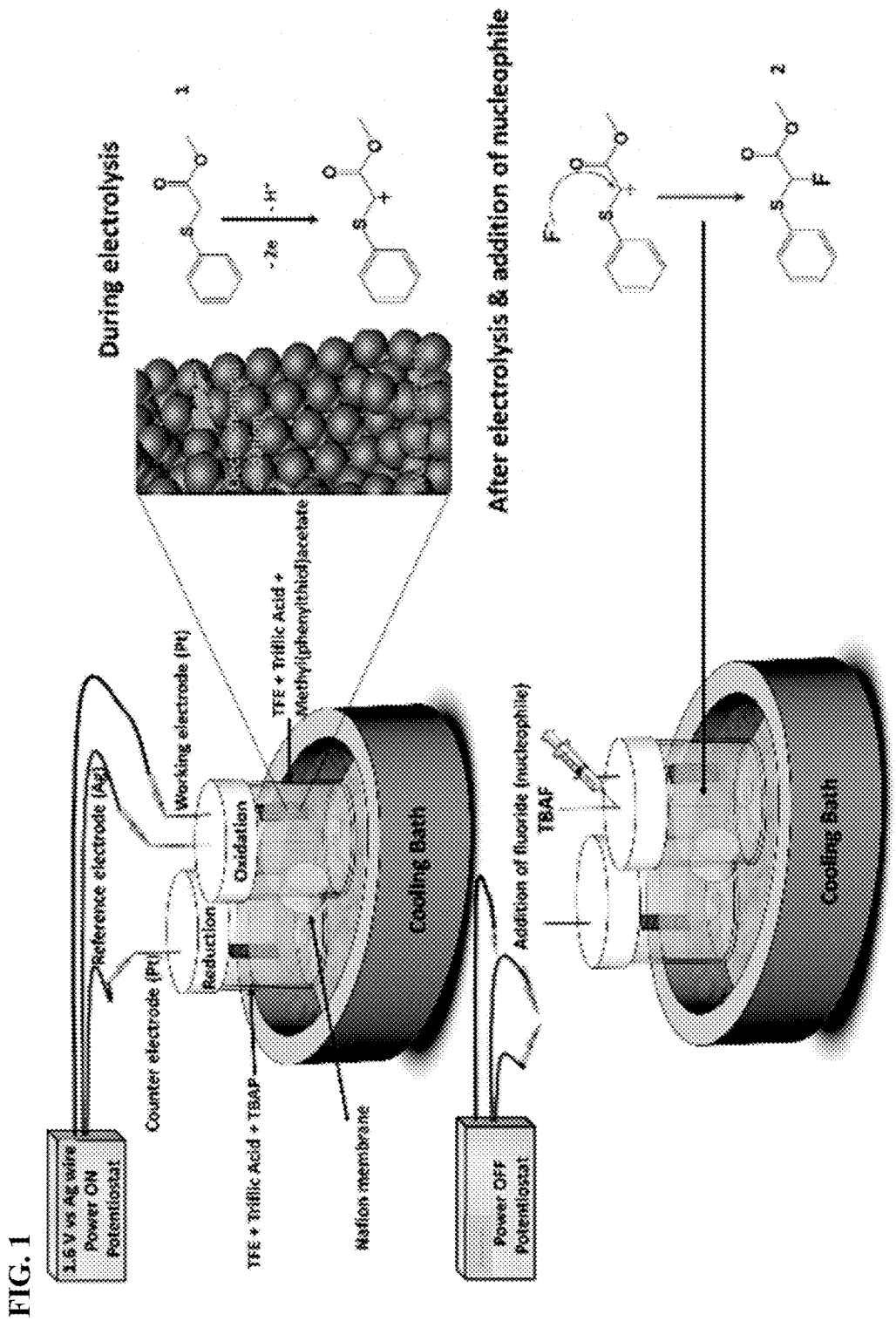
FIG. 1 shows a schematic of the cation pool method for fluorination of methyl-2-(phenylthiol)acetate.

Unless defined otherwise, technical and scientific terms used herein have the same meaning as commonly understood by a person of ordinary skill in the art. See, e.g., Singleton et al., Dictionary of Microbiology and Molecular Biology, 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

The term "electrochemical oxidation" as used herein refers to electron transfer to or from a molecule or ion, thereby changing its oxidation state. This reaction may occur, for example, through the application of an external voltage or the release of chemical energy. In aspects, electrochemical oxidation refers to the formation of a carbocation within an organic compound (e.g., removal of an electron to form a positively charged carbon atom). In aspects, electrochemical oxidation is performed from about 15 minutes to about 3 hours to form carbocations within the organic compounds. In aspects electrochemical oxidation is performed for about 30 minutes to about 2 hours to form carbocations within the organic compounds. In aspects electrochemical oxidation is performed for about 30 minutes to about 90 minutes to form carbocations within the organic compounds. In aspects electrochemical oxidation is performed for about 60 minutes to form carbocations within the organic compounds.

The term "oxidation state" as used herein means the hypothetical charge that an atom would have if all bonds to atoms of different elements were 100% ionic.

The term "carbocation" as used herein means a positively charged carbon atom. In other words, a carbocation is a carbon atom having only three bonds, resulting in a positive charge. Carbocations may be primary, secondary, or tertiary. In embodiments, a primary carbocation is a carbocation in which the carbon carrying the positive charge is only attached to one other alkyl group. In embodiments, a secondary carbocation is a carbocation in which the carbon carrying the positive charge is attached to two other alkyl groups, which may be the same group or different groups. In embodiments, a tertiary carbocation is a carbocation in which the carbon carrying the positive charge is attached to three alkyl groups, which may be any combination of same or different groups.

"Electron rich carbocation" refers to a positively charged carbon atom (i.e., carbocation) that is bound to another atom or atoms that are electron donating. Exemplary electron rich carbocations include carbocations that form part of an aromatic ring or a heteroaromatic ring when having a neutral charge (i.e., when not a carbocation); carbocations adjacent to a carbonyl carbon (e.g., carbonyl carbon forming part of an amide or ester); and carbocations adjacent to a sulfur atom or sulfur group.

"Carbocation stabilizing agent" refers to organic solvents, acids, bases, and combinations thereof that are capable of forming an anionic species that stabilize a carbocation without reacting with the carbocation. Methods of stabilizing carbocations include those methods described in Yoshida et al, J. Am. Chem. Soc., 121:9546-9549 (1999), the disclosure of which is incorporated by reference herein in its entirety.

The term "organic solvent" as used herein is used in accordance with its ordinary meaning in chemistry and refers to a solvent that is capable of stabilizing a carbocation within an organic compound without reacting with the carbocation. In aspects, the organic solvent is capable of forming an anionic species to stabilize the positively-charged carbocation. Non-limiting examples of organic solvents include trifluoroethanol, hexafluoroisopropanol, acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol/dimethyl ether), 1,2-dimethoxyethane (glyme/DME), dimethylformamide, dimethyl sulfoxide, 1,4-dioxane, ethanol, ethyl acetate, ethylene glycol, glycerin, heptane, hexamethylphosphoramide, hexamethylphosphorous triamide, hexane, methanol, methyl t-butyl ether, methylene chloride, N-methyl-2-pyrrolidinone, nitromethane, pentane, petroleum ether, 1-propanol, 2-propanol, pyridine, tetrahydrofuran, toluene, triethyl amine, o-xylene, m-xylene, or p-xylene. In embodiments, the organic solvent comprises trifluoroethanol, hexafluoroisopropanol, or a combination thereof.

The term "acid" as used herein refers to a strong acid that is capable of stabilizing a carbocation without reacting with the carbocation. In aspects, the acid can stabilize a carbocation in the absence of any additional compounds. In aspects, the acid can stabilize a carbocation in the presence of an organic solvent and/or a base. In aspects, the acid is capable of forming an anionic species to stabilize the positively-charged carbocation.

The term "base" as used herein refers to a strong base that is capable of stabilizing a carbocation without reacting with the carbocation. In aspects, the base can stabilize a carbocation in the absence of any additional compounds. In aspects, the base is capable of forming an anionic species to stabilize the positively-charged carbocation. In aspects, the base can stabilize a carbocation in the presence of an organic solvent and/or an acid. In aspects, the base is a non-nucleophilic base which is a sterically hindered organic base that is a poor nucleophile. Exemplary nucleophilic bases include N,N-diisopropylethylamine, 1,8-diazabicycloundec-7-ene, 1,5-diazabicyclo(4.3.0)non-5-ene, 2,6-di-ter-butylpyridine, phosphazene bases, lithium diisopropylamide, lithium tetramethylpiperidide, and conjugate bases of the acids described herein.

The term "nucleophile" as used herein refers to a chemical species that donates an electron pair to an electrophile (e.g., carbocation) to form a chemical bond in relation to a chemical reaction. All molecules or ions with a free pair of electrons, or at least one pi bond, may act as nucleophiles.

The term "fluorinated nucleophile" refers to a chemical species that donates a fluorine atom (e.g., $^{19}F$, $^{18}F$) to an electrophile (e.g., carbocation) to form a chemical bond in relation to a chemical reaction. In aspects, the fluorinated nucleophile has a single fluorine bound to a cationic species. In aspects, that cationic species of the fluorinated nucleophile is large, e.g., an atom with an atomic number of 19 or higher. In aspects, that cationic species of the fluorinated nucleophile is an atom with an atomic number of 35 or higher.

The term "radiofluorinated nucleophile" refers to a chemical species that donates a radioactive $^{18}F$-fluorine to an electrophile (e.g., carbocation) to form a chemical bond in relation to a chemical reaction. In aspects, the radioactive $^{18}F$-fluorinated nucleophile has an activity of at least 1 curie/millimole. In aspects, the ratio of $^{19}F$ (nonradioactive fluorine) to $^{18}F$ (radioactive fluorine) in the fluorinated nucleophile is at least 1,000 to 1. In aspects, the ratio of $^{19}F$ to $^{18}F$ in the fluorinated nucleophile is at least 10,000 to 1. In aspects, the ratio of $^{19}F$ to $^{18}F$ in the fluorinated nucleophile is at least 50,000 to 1.

The term "positron emission tomography" or "PET" as used herein means an imaging test that uses a radioactive substance (e.g., $^{18}F$-fluorine) to visualize tissue and organ functions. The radioactive substance may be injected, swallowed, or inhaled depending on the organ or tissue being studied.

The term "positron emission tomography radioligand" refers to radioactive substance (e.g., $^{18}F$-fluorine) that is used in a PET scan to visualize tissue and organ functions.

The term "radioligand" as used herein means a radioactive biochemical substance, in particular a ligand that is radiolabeled, capable of being used for diagnosis or research-oriented study of the receptor systems of the body.

The term "organic compound" as used herein refers to any of a class of chemical compounds in which one or more atoms of carbon are covalently linked to atoms of other elements, most commonly hydrogen, oxygen, sulfur, or nitrogen.

"Carbocationic organic compound" and "carbocation within an organic compound" refer to an organic compound that contains a carbocation.

The term "discontinuing electrochemical oxidation" as used herein refers to the process of stopping the electrochemical oxidation of the organic compound, e.g., when sufficient time has passed to form the carbocation within the organic compound. In aspects, electrochemical oxidation is performed from about 5 minutes to about 5 hours before it is discontinued. In aspects, electrochemical oxidation is performed from about 15 minutes to about 3 hours before it is discontinued. In aspects electrochemical oxidation is performed for about 30 minutes to about 2 hours before it is discontinued. In aspects electrochemical oxidation is performed for about 30 minutes to about 90 minutes before it is discontinued. In aspects electrochemical oxidation is performed for about 60 minutes before it is discontinued.

The term "saturated carbon atom" as used herein means a carbon atom bonded to as many hydrogen atoms as possible via single bonds.

The term "no-carrier added" as used herein refers to the use of the fluorinated and/or radiofluorinated nucleophiles described herein without any additional $^{19}F$-fluorine and/or $^{18}F$-fluorine sources involved in the process of fluorinating and/or radiofluorinating the organic compound. In aspects, the term "no-carrier added" means only one source of $^{19}F$-fluorine and/or $^{18}F$-fluorine is used in the process of fluorinating the organic compound (i.e., the process that occurs after producing a carbocation within the organic compound).

"Contacting" is used in accordance with its plain ordinary meaning and refers to the process of allowing at least two distinct species (e.g. chemical compounds such as an organic compound and a fluorinated nucleophile) to become sufficiently proximal to react, interact or physically touch. It should be appreciated; however, the resulting reaction product can be produced directly from a reaction between the added reagents or from an intermediate from one or more of the added reagents that can be produced in the reaction mixture. The phrase "adding a fluorinated nucleophile to the carbocation" refers to contacting a fluorinated nucleophile with a carbocation to allow the transfer of the fluorine from the fluorinated nucleophile to the carbocation, thereby covalently bonding the fluorine atom with the carbocation to form an fluorinated organic compound.

The abbreviations used herein have their conventional meaning within the chemical and biological arts. The chemical structures and formulae set forth herein are constructed according to the standard rules of chemical valency known in the chemical arts. Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇⌇" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

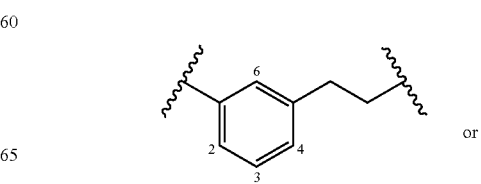

or

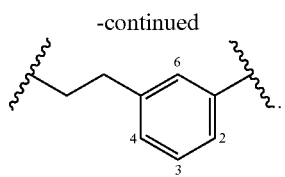

An alkylarylene moiety may be substituted (e.g. with a substituent group) on the alkylene moiety or the arylene linker (e.g. at carbons 2, 3, 4, or 6) with halogen, oxo, —N$_3$, —F$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) oxo, halogen, —CCl$_3$, —CBr$_3$, —CF$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from: (i) oxo, halogen, —CCl$_3$, —CBr$_3$, —CF$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from: (a) oxo, halogen, —CCl$_3$, —CBr$_3$, —CF$_3$, CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In embodiments, each substituted group described in the compounds herein is substituted with at least one substituent group. In aspects, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In aspects, at least one or all of these groups are substituted with at least one size-limited substituent group. In other embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted aryl ene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted aryl ene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms. The term "tautomer," as used herein, refers to one of two or more structural isomers which exist in equilibrium and which are readily converted from one isomeric form to another. It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$AG, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Methods

In embodiments, the disclosure provides methods for producing fluorinated organic compounds by performing electrochemical oxidation on the organic compound, thereby forming a carbocationic organic compound (i.e., a carbocation within an organic compound); and then adding a fluorinated nucleophile to the a carbocationic organic compound, thereby forming the fluorinated organic compound. "Adding a fluorinated nucleophile to the carbocation" refers to allowing the fluorinated nucleophile to contact the a carbocationic organic compound, thereby transferring the negatively-charged fluorine atom to the positively-charged carbocation to covalently bond the fluorine atom to the carbon atom to form the fluorinated organic compound. In aspects, the method of producing the fluorinated organic compound is performed by electrochemical oxidation in a double electrochemical cell or a multi-chamber electrochemical cell; wherein the electrochemical cell comprises an anodic cell and a cathodic cell separated by a cation exchange membrane or an anion exchange membrane. In aspects, the method of producing the fluorinated organic compound is performed in a flow-through platform. In aspects, the method of producing the fluorinated organic compound is performed in a microfluidic platform. In aspects, the electrochemical oxidation is cation pool formation.

In embodiments, the disclosure provides methods for producing fluorinated organic compounds by performing electrochemical oxidation on the organic compound, thereby forming a carbocationic organic compound (e.g., a carbocation within an organic compound); discontinuing (e.g., terminating) electrochemical oxidation; and then adding a fluorinated nucleophile to the a carbocationic organic compound, thereby forming the fluorinated organic compound. "Adding a fluorinated nucleophile to the carbocation" refers to contacting the fluorinated nucleophile with the a carbocationic organic compound, thereby transferring the negatively-charged fluorine atom to the positively-charged carbocation to covalently bond the fluorine atom to the carbon atom to form the fluorinated organic compound. In aspects, the method of producing the fluorinated organic compound is performed by electrochemical oxidation in a double electrochemical cell or a multi-chamber electrochemical cell; wherein the electrochemical cell comprises an anodic cell and a cathodic cell separated by a cation exchange membrane or an anion exchange membrane. In aspects, the method of producing the fluorinated organic compound is performed in a flow-through platform. In aspects, the method of producing the fluorinated organic compound is performed in a microfluidic platform. In aspects, the electrochemical oxidation is cation pool formation.

In embodiments, the disclosure provides methods for producing fluorinated organic compounds by performing electrochemical oxidation on the organic compound in the presence of a fluorinated nucleophile, wherein the electrochemical oxidation forms a carbocationic organic compound and the fluorinated nucleophile reacts with the carbocation of the a carbocationic organic compound to form fluorinated organic compound. In aspects, the method of producing the fluorinated organic compound is performed by electrochemical oxidation in a double electrochemical cell or a multi-chamber electrochemical cell; wherein the electrochemical cell comprises an anodic cell and a cathodic cell separated by a cation exchange membrane or an anion exchange membrane. In aspects, the method of producing the fluorinated organic compound is performed in a flow-through platform. In aspects, the method of producing the fluorinated organic compound is performed in a microfluidic platform. In aspects, the electrochemical oxidation is cation pool formation.

In embodiments, the electrochemical oxidation is performed in a liquid medium comprising the organic compound and an organic solvent, thereby forming a carbocationic organic compound (e.g., a carbocation within an organic compound). In aspects, the methods further comprise contacting a fluorinated nucleophile with the carbocationic organic compound, thereby forming the fluorinated organic compound. In aspects, the methods further comprise discontinuing (e.g., terminating) electrochemical oxidation; and then contacting a fluorinated nucleophile with the carbocationic organic compound, thereby forming the fluorinated organic compound. In aspects, the organic solvent is present in an amount effective to stabilize the carbocation formed by the electrochemical oxidation of the organic compound, i.e., the organic solvent is capable of stabilizing the a carbocationic organic compound without reacting with the carbocation. In aspects, the organic solvent is a mixture of trifluoroethanol and hexafluoroisopropanol. In aspects, the organic solvent is trifluoroethanol. In aspects, the organic solvent is hexafluoroisopropanol.

In embodiments, electrochemical oxidation is performed in a liquid medium comprising the organic compound, an organic solvent, and an acid, thereby forming a carbocationic organic compound (e.g., a carbocation within an organic compound). In aspects, the methods further comprise contacting a fluorinated nucleophile with the carbocationic organic compound, thereby forming the fluorinated organic compound. In aspects, the methods further comprise discontinuing (e.g., terminating) electrochemical oxidation; and then contacting a fluorinated nucleophile with the carbocationic organic compound, thereby forming the fluorinated organic compound. In aspects, the organic solvent and acid are present in an amount effective to stabilize the carbocation formed by the electrochemical oxidation of the organic compound, i.e., the organic solvent and the acid are capable of stabilizing the a carbocationic organic compound without reacting with the carbocation. In aspects, the organic solvent is a mixture of trifluoroethanol and hexafluoroisopropanol. In aspects, the organic solvent is trifluoroethanol. In aspects, the organic solvent is hexafluoroisopropanol. In aspects, the acid is trifluoromethanesulfonic acid, tetrabutylammonium perchlorate, tetrabutylammonium tetrafluoroborate, trifluoroacetic acid, p-toluenesulfonic acid, or a combination thereof. In aspects the acid is a mixture of trifluoromethanesulfonic acid and tetrabutylammonium perchlorate. In aspects the acid is trifluoromethanesulfonic acid. In aspects the acid is tetrabutylammonium perchlorate. In aspects, the organic solvent is trifluoroethanol and the acid is trifluoromethanesulfonic acid. In aspects, the organic solvent is trifluoroethanol and the acid is tetrabutylammonium perchlorate. In aspects, the organic solvent is trifluoroethanol and the acid is a mixture of trifluoromethanesulfonic acid and tetrabutylammonium perchlorate. In aspects, the organic solvent is hexafluoroisopropanol and the acid is trifluoromethanesulfonic acid. In aspects, the organic solvent is hexafluoroisopropanol and the acid is tetrabutylammonium perchlorate. In aspects, the organic solvent is hexafluoroisopropanol and the acid is a mixture of trifluoromethanesulfonic acid and tetrabutylammonium perchlorate. In aspects, the organic solvent is a mixture of trifluoroethanol and hexafluoroisopropanol and the acid is trifluoromethanesulfonic acid. In aspects, the organic solvent is a mixture of trifluoroethanol and hexafluoroisopropanol and the acid is tetrabutylammonium perchlorate. In aspects, the organic solvent is a mixture of trifluoroethanol and hexafluoroisopropanol and the acid is a mixture of trifluoromethanesulfonic acid and tetrabutylammonium perchlorate. In aspects, the molar ratio of the organic solvent to the acid is from about 0.5 to about 5. In aspects, the molar ratio of the organic solvent to the acid is from about 0.8 to about 3. In aspects, the molar ratio of the organic solvent to the acid is from about 0.8 to about 2. In aspects, the molar ratio of the organic solvent to the acid is from about 0.9 to about 1.5. In aspects, the molar ratio of the organic solvent to the acid is from about 0.9 to about 1.4. In aspects, the molar ratio of the organic solvent to the acid is from about 0.9 to about 1.3. In aspects, the molar ratio of the organic solvent to the acid is from about 1 to about 1.3. In aspects, the molar ratio of the organic solvent to the acid is from about 1 to about 1.2. In aspects, the molar ratio of the organic solvent to the acid is from about 1.1 to about 1.2. In aspects, the molar ratio of the organic solvent to the acid is from about 1.1 to about 1.3.

In embodiments, electrochemical oxidation is performed in a liquid medium comprising the organic compound, an organic solvent, and a base, thereby forming a carbocationic organic compound (e.g., a carbocation within an organic compound). In aspects, the methods further comprise contacting a fluorinated nucleophile with the carbocationic organic compound, thereby forming the fluorinated organic compound. In aspects, the methods further comprise discontinuing (e.g., terminating) electrochemical oxidation; and then contacting a fluorinated nucleophile with the carbocationic organic compound, thereby forming the fluorinated organic compound. In aspects, the organic solvent and base are present in an amount effective to stabilize the carbocation formed by the electrochemical oxidation of the organic compound, i.e., the organic solvent and the base are capable of stabilizing the a carbocationic organic compound without reacting with the carbocation. In aspects, the base is a non-nucleophilic base. In aspects, the organic solvent is a mixture of trifluoroethanol and hexafluoroisopropanol. In aspects, the organic solvent is trifluoroethanol. In aspects, the organic solvent is hexafluoroisopropanol. In aspects, the base is a non-nucleophilic base. In aspects, the base is a conjugate base of trifluoromethanesulfonic acid, a conjugate base of tetrabutylammonium perchlorate, a conjugate base of tetrabutylammonium tetrafluoroborate, trifluoroacetic acid, a conjugate base of p-toluenesulfonic acid, or a combination thereof.

In embodiments, electrochemical oxidation is performed in a liquid medium comprising the organic compound, an organic solvent, an acid, and a base, thereby forming a carbocationic organic compound (e.g., a carbocation within an organic compound). In aspects, the methods further comprise contacting a fluorinated nucleophile with the carbocationic organic compound, thereby forming the fluorinated organic compound. In aspects, the methods further comprise discontinuing (e.g., terminating) electrochemical oxidation; and then contacting a fluorinated nucleophile with the carbocationic organic compound, thereby forming the fluorinated organic compound. In aspects, the organic solvent, acid, and base are present in an amount effective to stabilize the carbocation formed by the electrochemical oxidation of the organic compound, i.e., the organic solvent, the acid, and the base are capable of stabilizing the a carbocationic organic compound without reacting with the carbocation. In aspects, the organic solvent is a mixture of trifluoroethanol and hexafluoroisopropanol. In aspects, the organic solvent is trifluoroethanol. In aspects, the organic solvent is hexafluoroisopropanol. In aspects, the acid is trifluoromethanesulfonic acid, tetrabutylammonium perchlorate, tetrabutylammonium tetrafluoroborate, trifluoroacetic acid, p-toluenesulfonic acid, or a combination thereof. In aspects the acid is a mixture of trifluoromethanesulfonic acid and tetrabutylammonium perchlorate. In aspects the acid is trifluoromethanesulfonic acid. In aspects the acid is tetrabutylammonium perchlorate. In aspects, the organic solvent is trifluoroethanol and the acid is trifluoromethanesulfonic acid. In aspects, the organic solvent is trifluoroethanol and the acid is tetrabutylammonium perchlorate. In aspects, the organic solvent is trifluoroethanol and the acid is a mixture of trifluoromethanesulfonic acid and tetrabutylammonium perchlorate. In aspects, the organic solvent is hexafluoroisopropanol and the acid is trifluoromethanesulfonic acid. In aspects, the organic solvent is hexafluoroisopropanol and the acid is tetrabutylammonium perchlorate. In aspects, the organic solvent is hexafluoroisopropanol and the acid is a mixture of trifluoromethanesulfonic acid and tetrabutylammonium perchlorate. In aspects, the organic solvent is a mixture of trifluoroethanol and hexafluoroisopropanol and the acid is trifluoromethanesulfonic acid. In aspects, the organic solvent is a mixture of trifluoroethanol and hexafluoroisopropanol and the acid is tetrabutylammonium perchlorate. In aspects, the organic solvent is a mixture of trifluoroethanol and hexafluoroisopropanol and the acid is a mixture of trifluoromethanesulfonic acid and tetrabutylammonium perchlorate. In aspects, the base is a non-nucleophilic base. In aspects, the base is a conjugate base of trifluoromethanesulfonic acid, a conjugate base of tetrabutylammonium perchlorate, a conjugate base of tetrabutylammonium tetrafluoroborate, trifluoroacetic acid, a conjugate base of p-toluenesulfonic acid, or a combination thereof.

In embodiments, electrochemical oxidation is performed in a liquid medium comprising the organic compound and an acid, thereby forming a carbocationic organic compound (e.g., a carbocation within an organic compound). In aspects, the methods further comprise contacting a fluorinated nucleophile with the carbocationic organic compound, thereby forming the fluorinated organic compound. In aspects, the methods further comprise discontinuing (e.g., terminating) electrochemical oxidation; and then contacting a fluorinated nucleophile with the carbocationic organic compound, thereby forming the fluorinated organic compound. In aspects, the acid is present in an amount effective to stabilize the carbocation formed by the electrochemical oxidation of the organic compound, i.e., the acid is capable of stabilizing the a carbocationic organic compound without reacting with the carbocation. In aspects, the acid is trifluoromethanesulfonic acid, tetrabutylammonium perchlorate, tetrabutylammonium tetrafluoroborate, trifluoroacetic acid, p-toluenesulfonic acid, or a combination thereof. In aspects the acid is a mixture of trifluoromethanesulfonic acid and tetrabutylammonium perchlorate. In aspects the acid is trifluoromethanesulfonic acid. In aspects the acid is tetrabutylammonium perchlorate.

In embodiments, electrochemical oxidation is performed in a liquid medium comprising the organic compound and a base, thereby forming a carbocationic organic compound (e.g., a carbocation within an organic compound). In aspects, the methods further comprise contacting a fluorinated nucleophile with the carbocationic organic compound, thereby forming the fluorinated organic compound. In aspects, the methods further comprise discontinuing (e.g., terminating) electrochemical oxidation; and then contacting a fluorinated nucleophile with the carbocationic organic compound, thereby forming the fluorinated organic compound. In aspects, the base is present in an amount effective to stabilize the carbocation formed by the electrochemical oxidation of the organic compound, i.e., the base is capable of stabilizing the a carbocationic organic compound without reacting with the carbocation. In aspects, the base is a non-nucleophilic base. In aspects, the base is a conjugate base of trifluoromethanesulfonic acid, a conjugate base of tetrabutylammonium perchlorate, a conjugate base of tetrabutylammonium tetrafluoroborate, trifluoroacetic acid, a conjugate base of p-toluenesulfonic acid, or a combination thereof.

In embodiments, electrochemical oxidation is performed in a liquid medium comprising the organic compound, an acid, and a base, thereby forming a carbocationic organic compound (e.g., a carbocation within an organic compound). In aspects, the methods further comprise contacting a fluorinated nucleophile with the carbocationic organic compound, thereby forming the fluorinated organic compound. In aspects, the methods further comprise discontinuing (e.g., terminating) electrochemical oxidation; and then contacting a fluorinated nucleophile with the carbocationic organic compound, thereby forming the fluorinated organic compound. In aspects, the acid and base are present in an amount effective to stabilize the carbocation formed by the electrochemical oxidation of the organic compound, i.e., the acid and the base are capable of stabilizing the a carbocationic organic compound without reacting with the carbocation. In aspects, the base is a non-nucleophilic base. In aspects, the acid is trifluoromethanesulfonic acid, tetrabutylammonium perchlorate, tetrabutylammonium tetrafluoroborate, trifluoroacetic acid, p-toluenesulfonic acid, or a combination thereof. In aspects the acid is a mixture of trifluoromethanesulfonic acid and tetrabutylammonium perchlorate. In aspects the acid is trifluoromethanesulfonic acid. In aspects the acid is tetrabutylammonium perchlorate. In aspects, the base is a non-nucleophilic base. In aspects, the base is a conjugate base of trifluoromethanesulfonic acid, a conjugate base of tetrabutylammonium perchlorate, a conjugate base of tetrabutylammonium tetrafluoroborate, trifluoroacetic acid, a conjugate base of p-toluenesulfonic acid, or a combination thereof.

In embodiments, the fluorination of the organic compound is performed in a liquid medium comprising a fluorinated nucleophile, a carbocationic organic compound, and an organic solvent. In aspects, the fluorination of the organic compound is performed after termination of the electrochemical oxidation. In aspects, the organic solvent is present in an amount effective to stabilize the carbocationic organic compound without reacting with the carbocation. In aspects, the fluorinated nucleophile is an $^{18}$F-fluorinated nucleophile. In aspects, the fluorinated nucleophile is an $^{19}$F-fluorinated nucleophile. In aspects, the fluorinated nucleophile comprises an $^{18}$F-fluorine, an $^{19}$F-fluorine, or a combination thereof. In aspects, the organic solvent is a mixture of trifluoroethanol and hexafluoroisopropanol. In aspects, the organic solvent is trifluoroethanol. In aspects, the organic solvent is hexafluoroisopropanol.

In embodiments, the fluorination of the organic compound is performed in a liquid medium comprising a fluorinated nucleophile, a carbocationic organic compound, an organic solvent, and an acid. In aspects, the fluorination of the organic compound is performed after termination of the electrochemical oxidation. In aspects, the organic solvent and acid are present in an amount effective to stabilize the carbocationic organic compound without reacting with the carbocation. In aspects, the fluorinated nucleophile is an $^{18}$F-fluorinated nucleophile. In aspects, the fluorinated nucleophile is an $^{19}$F-fluorinated nucleophile. In aspects, the fluorinated nucleophile comprises an $^{18}$F-fluorine, an $^{19}$F-fluorine, or a combination thereof. In aspects, the organic solvent is a mixture of trifluoroethanol and hexafluoroisopropanol. In aspects, the organic solvent is trifluoroethanol. In aspects, the organic solvent is hexafluoroisopropanol. In aspects, the acid is trifluoromethanesulfonic acid, tetrabutylammonium perchlorate, tetrabutylammonium tetrafluoroborate, trifluoroacetic acid, p-toluenesulfonic acid, or a combination thereof. In aspects the acid is a mixture of trifluoromethanesulfonic acid and tetrabutylammonium perchlorate. In aspects the acid is trifluoromethanesulfonic acid. In aspects the acid is tetrabutylammonium perchlorate. In aspects, the organic solvent is trifluoroethanol and the acid is trifluoromethanesulfonic acid. In aspects, the organic solvent is trifluoroethanol and the acid is tetrabutylammonium perchlorate. In aspects, the organic solvent is trifluoroethanol and the acid is a mixture of trifluoromethanesulfonic acid and tetrabutylammonium perchlorate. In aspects, the organic solvent is hexafluoroisopropanol and the acid is trifluoromethanesulfonic acid. In aspects, the organic solvent is hexafluoroisopropanol and the acid is tetrabutylammonium perchlorate. In aspects, the organic solvent is hexafluoroisopropanol and the acid is a mixture of trifluoromethanesulfonic acid and tetrabutylammonium perchlorate. In aspects, the organic solvent is a mixture of trifluoroethanol and hexafluoroisopropanol and the acid is trifluoromethanesulfonic acid. In aspects, the organic solvent is a mixture of trifluoroethanol and hexafluoroisopropanol and the acid is tetrabutylammonium perchlorate. In aspects, the organic solvent is a mixture of trifluoroethanol and hexafluoroisopropanol and the acid is a mixture of trifluoromethanesulfonic acid and tetrabutylammonium perchlorate. In aspects, the molar ratio of the organic solvent to the acid is from about 0.5 to about 5. In aspects, the molar ratio of the organic solvent to the acid is from about 0.8 to about 3. In aspects, the molar ratio of the organic solvent to the acid is from about 0.8 to about 2. In aspects, the molar ratio of the organic solvent to the acid is from about 0.9 to about 1.5. In aspects, the molar ratio of the organic solvent to the acid is from about 0.9 to about 1.4. In aspects, the molar ratio of the organic solvent to the acid is from about 0.9 to about 1.3. In aspects, the molar ratio of the organic solvent to the acid is from about 1 to about 1.3. In aspects, the molar ratio of the organic solvent to the acid is from about 1 to about 1.2. In aspects, the molar ratio of the organic solvent to the acid is from about 1.1 to about 1.2. In aspects, the molar ratio of the organic solvent to the acid is from about 1.1 to about 1.3.

In embodiments, the fluorination of the organic compound is performed in a liquid medium comprising a fluorinated nucleophile, a carbocationic organic compound, an organic solvent, and a base. In aspects, the fluorination of the organic compound is performed after termination of the electrochemical oxidation. In aspects, the organic solvent and base are present in an amount effective to stabilize the carbocationic organic compound without reacting with the carbocation. In aspects, the fluorinated nucleophile is an $^{18}$F-fluorinated nucleophile. In aspects, the fluorinated nucleophile is an $^{19}$F-fluorinated nucleophile. In aspects, the fluorinated nucleophile comprises an $^{18}$F-fluorine, an $^{19}$F-fluorine, or a combination thereof. In aspects, the base is a non-nucleophilic base. In aspects, the organic solvent is a mixture of trifluoroethanol and hexafluoroisopropanol. In aspects, the organic solvent is trifluoroethanol. In aspects, the organic solvent is hexafluoroisopropanol. In aspects, the base is a non-nucleophilic base. In aspects, the base is a conjugate base of trifluoromethanesulfonic acid, a conjugate base of tetrabutylammonium perchlorate, a conjugate base of tetrabutylammonium tetrafluoroborate, trifluoroacetic acid, a conjugate base of p-toluenesulfonic acid, or a combination thereof.

In embodiments, the fluorination of the organic compound is performed in a liquid medium comprising a fluorinated nucleophile, a carbocationic organic compound, an organic solvent, an acid, and a base. In aspects, the fluorination of the organic compound is performed after termination of the electrochemical oxidation. In aspects, the organic solvent, acid, and base are present in an amount effective to stabilize the carbocationic organic compound without reacting with the carbocation. In aspects, the fluorinated nucleophile is an $^{18}$F-fluorinated nucleophile. In aspects, the fluorinated nucleophile is an $^{19}$F-fluorinated nucleophile. In aspects, the fluorinated nucleophile comprises an $^{18}$F-fluorine, an $^{19}$F-fluorine, or a combination thereof. In aspects, the organic solvent is a mixture of trifluoroethanol and hexafluoroisopropanol. In aspects, the organic solvent is trifluoroethanol. In aspects, the organic solvent is hexafluoroisopropanol. In aspects, the acid is trifluoromethanesulfonic acid, tetrabutylammonium perchlorate, tetrabutylammonium tetrafluoroborate, trifluoroacetic acid, p-toluenesulfonic acid, or a combination thereof. In aspects the acid is a mixture of trifluoromethanesulfonic acid and tetrabutylammonium perchlorate. In aspects the acid is trifluoromethanesulfonic acid. In aspects the acid is tetrabutylammonium perchlorate. In aspects, the organic solvent is trifluoroethanol and the acid is trifluoromethanesulfonic acid. In aspects, the organic solvent is trifluoroethanol and the acid is tetrabutylammonium perchlorate. In aspects, the organic solvent is trifluoroethanol and the acid is a mixture of trifluoromethanesulfonic acid and tetrabutylammonium perchlorate. In aspects, the organic solvent is hexafluoroisopropanol and the acid is trifluoromethanesulfonic acid. In aspects, the organic solvent is hexafluoroisopropanol and the acid is tetrabutylammonium perchlorate. In aspects, the organic solvent is hexafluoroisopropanol and the acid is a mixture of trifluoromethanesulfonic acid and tetrabutylammonium perchlorate. In aspects, the organic solvent is a mixture of trifluoroethanol and hexafluoroisopropanol and the acid is trifluoromethanesulfonic acid. In aspects, the organic solvent is a mixture of trifluoroethanol and hexafluoroisopropanol and the acid is tetrabutylammonium perchlorate. In aspects, the organic solvent is a mixture of trifluoroethanol and hexafluoroisopropanol and the acid is a mixture of trifluoromethanesulfonic acid and tetrabutylammonium perchlorate. In aspects, the base is a non-nucleophilic base. In aspects, the base is a conjugate base of trifluoromethanesulfonic acid, a conjugate base of tetrabutylammonium perchlorate, a conjugate base of tetrabutylammonium tetrafluoroborate, trifluoroacetic acid, a conjugate base of p-toluenesulfonic acid, or a combination thereof.

In embodiments, the fluorination of the organic compound is performed in a liquid medium comprising a fluorinated nucleophile, a carbocationic organic compound, and an acid. In aspects, the fluorination of the organic compound is performed after termination of the electrochemical oxidation. In aspects, the acid is present in an amount effective to stabilize the carbocationic organic compound without reacting with the carbocation. In aspects, the fluorinated nucleophile is an $^{18}$F-fluorinated nucleophile. In aspects, the fluorinated nucleophile is an $^{19}$F-fluorinated nucleophile. In aspects, the fluorinated nucleophile comprises an $^{18}$F-fluorine, an $^{19}$F-fluorine, or a combination thereof. In aspects, the acid is trifluoromethanesulfonic acid, tetrabutylammonium perchlorate, tetrabutylammonium tetrafluoroborate, trifluoroacetic acid, p-toluenesulfonic acid, or a combination thereof. In aspects the acid is a mixture of trifluoromethanesulfonic acid and tetrabutylammonium perchlorate. In aspects the acid is trifluoromethanesulfonic acid. In aspects the acid is tetrabutylammonium perchlorate.

In embodiments, the fluorination of the organic compound is performed in a liquid medium comprising a fluorinated nucleophile, a carbocationic organic compound, and a base. In aspects, the fluorination of the organic compound is performed after termination of the electrochemical oxidation. In aspects, the base is present in an amount effective to stabilize the carbocationic organic compound without reacting with the carbocation. In aspects, the fluorinated nucleophile is an $^{18}$F-fluorinated nucleophile. In aspects, the fluorinated nucleophile is an $^{19}$F-fluorinated nucleophile. In aspects, the fluorinated nucleophile comprises an $^{18}$F-fluorine, an $^{19}$F-fluorine, or a combination thereof. In aspects, the base is a non-nucleophilic base. In aspects, the base is a conjugate base of trifluoromethanesulfonic acid, a conjugate base of tetrabutylammonium perchlorate, a conjugate base of tetrabutylammonium tetrafluoroborate, trifluoroacetic acid, a conjugate base of p-toluenesulfonic acid, or a combination thereof.

In embodiments, the fluorination of the organic compound is performed in a liquid medium comprising a fluorinated nucleophile, a carbocationic organic compound, an acid, and a base. In aspects, the fluorination of the organic compound is performed after termination of the electrochemical oxidation. In aspects, the acid and base are present in an amount effective to stabilize the carbocationic organic compound without reacting with the carbocation. In aspects, the fluorinated nucleophile is an $^{18}$F-fluorinated nucleophile. In aspects, the fluorinated nucleophile is an $^{19}$F-fluorinated nucleophile. In aspects, the fluorinated nucleophile comprises an $^{18}$F-fluorine, and $^{19}$F-fluorine, or a combination thereof. In aspects, the acid is trifluoromethanesulfonic acid, tetrabutylammonium perchlorate, tetrabutylammonium tetrafluoroborate, trifluoroacetic acid, p-toluenesulfonic acid, or a combination thereof. In aspects the acid is a mixture of trifluoromethanesulfonic acid and tetrabutylammonium perchlorate. In aspects the acid is trifluoromethanesulfonic acid. In aspects the acid is tetrabutylammonium perchlorate. In aspects, the base is a non-nucleophilic base. In aspects, the base is a conjugate base of trifluoromethanesulfonic acid, conjugate base of tetrabutylammonium perchlorate, a conjugate base of tetrabutylammonium tetrafluoroborate, trifluoroacetic acid, a conjugate base of p-toluenesulfonic acid, or a combination thereof.

In embodiments, the fluorinated nucleophile is any compound capable of donating a fluorine atom to the carbocation of a carbocationic organic compound when they come into contact with each other, i.e., when the fluorinated nucleophile is added to the reaction mixture with the carbocationic organic compound. In aspects, the fluorinated nucleophile comprises a single fluorine (e.g., $^{18}F$ or $^{19}F$) bound to a cationic species. In aspects, the fluorinated nucleophile comprises a cationic species that has a +1 charge. In aspects, the fluorinated nucleophile comprises a large cationic species, i.e., an atom with atomic number 19 or higher. In aspects, the fluorinated nucleophile comprises a cationic species that has an atom with an atomic number of 35 or higher. In aspects, the cationic species contains more than one atom with MW 35 or higher. In aspects, the fluorinated nucleophile comprises $K(^{18}F)F—K_{222}$, cesium fluoride, potassium fluoride, triethylamine trihydrofluoride, or tetrabutylammonium fluoride. In aspects, the fluorinated nucleophile comprises at least two compounds selected from the group consisting of $K(^{18}F)F—K_{222}$, cesium fluoride, potassium fluoride, triethylamine trihydrofluoride, or tetrabutylammonium fluoride. In aspects, the fluorinated nucleophile comprises $K(^{18}F)F—K_{222}$. In aspects, the fluorinated nucleophile comprises cesium fluoride. In aspects, the fluorinated nucleophile comprises potassium fluoride. In aspects, the fluorinated nucleophile comprises triethylamine trihydrofluoride. In aspects, the fluorinated nucleophile comprises tetrabutylammonium fluoride. In aspects, the fluorinated nucleophile comprises $K(^{18}F)F—K_{222}$ and cesium fluoride. In aspects, the fluorinated nucleophile comprises $K(^{18}F)F—K_{222}$ and potassium fluoride. In aspects, the fluorinated nucleophile comprises $K(^{18}F)F—K_{222}$ and triethylamine trihydrofluoride. In aspects, the fluorinated nucleophile comprises $K(^{18}F)F—K_{222}$ and tetrabutylammonium fluoride. In aspects, the fluorinated nucleophile comprises cesium fluoride and potassium fluoride. In aspects, the fluorinated nucleophile comprises cesium fluoride and triethylamine trihydrofluoride. In aspects, the fluorinated nucleophile comprises cesium fluoride and tetrabutylammonium fluoride. In aspects, the fluorinated nucleophile comprises potassium fluoride and triethylamine trihydrofluoride. In aspects, the fluorinated nucleophile comprises potassium fluoride and tetrabutylammonium fluoride. In aspects, the fluorinated nucleophile comprises triethylamine trihydrofluoride and tetrabutylammonium fluoride. In aspects, the fluorinated nucleophile does not comprise a thiofluorine group.

In embodiments, the fluorinated nucleophile is any compound capable of donating a radioactive $^{18}F$-fluorine atom to the carbocation of an organic compound when they come into contact with each other, i.e., when the $^{18}F$-fluorinated nucleophile is added to the reaction mixture with the carbocationic organic compound. In aspects, the radioactive $^{18}F$-fluorinated nucleophile has an activity of at least 1 curie/millimole. In aspects, the ratio of $^{19}F$-fluorine (nonradioactive) to $^{18}F$-fluorine (radioactive) in the fluorinated nucleophile (or in a plurality of fluorinated nucleophiles) is at least 1000 to 1. In aspects, the ratio of $^{19}F$-fluorine (nonradioactive) to $^{18}F$-fluorine (radioactive) in the fluorinated nucleophile (or in a plurality of fluorinated nucleophiles) is at least 10,000 to 1. In aspects, the ratio of $^{19}F$-fluorine (nonradioactive) to $^{18}F$-fluorine (radioactive) in the fluorinated nucleophile (or in a plurality of fluorinated nucleophiles) is at least 50,000 to 1. In aspects, the radiofluorinated nucleophile comprises $K(^{18}F)F—K_{222}$, $(^{18}F)$cesium fluoride, $(^{18}F)$potassium fluoride, $(^{18}F)$triethylamine trihydrofluoride, or $(^{18}F)$tetrabutylammonium fluoride. In aspects, the fluorinated nucleophile comprises at least two compounds selected from the group consisting of $K(^{18}F)F—K_{222}$, $(^{18}F)$cesium fluoride, $(^{18}F)$potassium fluoride, $(^{18}F)$triethylamine trihydrofluoride, and $(^{18}F)$tetrabutylammonium fluoride. In aspects, the fluorinated nucleophile comprises $K(^{18}F)F—K_{222}$. In aspects, the fluorinated nucleophile comprises $(^{18}F)$cesium fluoride. In aspects, the fluorinated nucleophile comprises $(^{18}F)$potassium fluoride. In aspects, the fluorinated nucleophile comprises $(^{18}F)$triethylamine trihydrofluoride. In aspects, the fluorinated nucleophile comprises $(^{18}F)$tetrabutylammonium fluoride. In aspects, the fluorinated nucleophile comprises $K(^{18}F)F—K_{222}$ and $(^{18}F)$cesium fluoride. In aspects, the fluorinated nucleophile comprises $K(^{18}F)F—K_{222}$ and $(^{18}F)$potassium fluoride. In aspects, the fluorinated nucleophile comprises $K(^{18}F)F—K_{222}$ and $(^{18}F)$triethylamine trihydrofluoride. In aspects, the fluorinated nucleophile comprises $K(^{18}F)F—K_{222}$ and $(^{18}F)$tetrabutylammonium fluoride. In aspects, the fluorinated nucleophile comprises $(^{18}F)$cesium fluoride and $(^{18}F)$potassium fluoride. In aspects, the fluorinated nucleophile comprises $(^{18}F)$cesium fluoride and $(^{18}F)$triethylamine trihydrofluoride. In aspects, the fluorinated nucleophile comprises $(^{18}F)$cesium fluoride and $(^{18}F)$tetrabutylammonium fluoride. In aspects, the fluorinated nucleophile comprises $(^{18}F)$potassium fluoride and $(^{18}F)$triethylamine trihydrofluoride. In aspects, the fluorinated nucleophile comprises $(^{18}F)$potassium fluoride and $(^{18}F)$tetrabutylammonium fluoride. In aspects, the fluorinated nucleophile comprises $(^{18}F)$triethylamine trihydrofluoride and $(^{18}F)$tetrabutylammonium fluoride. In aspects, the fluorinated nucleophile does not comprise a thiofluorine group.

In embodiments, the fluorinated nucleophile is a no-carrier added fluorinated nucleophile, i.e., there are no other fluorine sources involved in fluorinating the carbocationic organic compound other than the fluorinated nucleophile. In aspects, only one fluorinated nucleophile is used in the step of fluorinating the carbocationic organic compound. In aspects, only a fluorinated nucleophile, and not a radiofluorinated nucleophile, is used in the step of fluorinating the carbocationic organic compound. In embodiments, the radiofluorinated nucleophile is a no-carrier added radiofluorinated nucleophile, i.e., there are no other radioactive fluorine sources involved in radiofluorinating the carbocationic organic compound other than the radiofluorinated nucleophile. In aspects, only one radiofluorinated nucleophile is used in the step of radiofluorinating the carbocationic organic compound. In aspects, only a radiofluorinated nucleophile, and not a non-radiofluorinated nucleophile, is used in the step of fluorinating the carbocationic organic compound. In aspects, only one fluorinated nucleophile is used in the step of fluorinating the carbocationic organic compound, where some of those fluorinated nucleophile have an $^{18}F$-fluorine and some of the fluorinated nucleophile have an $^{19}F$-fluorine, and where the ratio of the $^{19}F$ to $^{18}F$ is at least 1000 to 1. In aspects, the only fluorine source used to fluorinate the carbocation of the organic compound is $K(^{18}F)F—K_{222}$. In aspects, the only fluorine source used to fluorinate the carbocation of the organic compound is cesium fluoride. In aspects, the only fluorine source used to fluorinate the carbocation of the organic compound is potassium fluoride. In aspects, the only fluorine source used to fluorinate the carbocation of the organic compound is triethylamine trihydrofluoride. In aspects, the only fluorine source used to fluorinate the carbocation of the organic compound is tetrabutylammonium fluoride. In aspects, the only fluorine source used to fluorinate the carbocation of the organic compound is ($^{18}$F)cesium fluoride. In aspects, the only fluorine source used to fluorinate the carbocation of the organic compound is ($^{18}$F)potassium fluoride. In aspects, the only fluorine source used to fluorinate the carbocation of the organic compound is ($^{18}$F)triethylamine trihydrofluoride. In aspects, the only fluorine source used to fluorinate the carbocation of the organic compound is ($^{18}$F)tetrabutylammonium fluoride. In aspects, the only fluorine sources used to fluorinate the carbocation of the organic compound are cesium fluoride and ($^{18}$F)cesium fluoride. In aspects, the only fluorine sources used to fluorinate the carbocation of the organic compound are potassium fluoride and ($^{18}$F) potassium fluoride. In aspects, the only fluorine sources used to fluorinate the carbocation of the organic compound are triethylamine trihydrofluoride and ($^{18}$F)triethylamine trihydrofluoride. In aspects, the only fluorine sources used to fluorinate the carbocation of the organic compound are tetrabutylammonium fluoride and ($^{18}$F)tetrabutylammonium fluoride. In aspects, only the non-radioactive nucleophile is used as the source of fluorine, and radioactive nucleophiles are not used. In aspects, only the radioactive nucleophile is used as the source of the fluorine, and non-radioactive nucleophiles are not used.

In embodiments, the fluorinated nucleophile is a no-carrier added fluorinated nucleophile, i.e., there are no other fluorine sources involved in fluorinating the carbocationic organic compound other than the fluorinated nucleophile. In aspects, the only fluorine source used to fluorinate the carbocation of the organic compound is cesium fluoride, wherein the cesium fluoride compounds contain $^{19}$F-fluorine or $^{18}$F-fluorine, provided that some of the cesium fluoride compounds used in the process contain $^{19}$F-fluorine and some of the cesium fluoride compounds used in the process contain $^{18}$F-fluorine. In aspects, the ratio of the $^{19}$F to $^{18}$F in the cesium fluoride compounds used in the process is at least 1000 to 1. In aspects, the only fluorine source used to fluorinate the carbocation of the organic compound is potassium fluoride, wherein the potassium fluoride compounds contain either $^{19}$F-fluorine or $^{18}$F-fluorine, provided that some of the potassium fluoride compounds used in the process contain $^{19}$F-fluorine and some of the potassium fluoride compounds used in the process contain $^{18}$F-fluorine. In aspects, the ratio of the $^{19}$F to $^{18}$F in the potassium fluoride compounds used in the process is at least 1000 to 1. In aspects, the only fluorine source used to fluorinate the carbocation of the organic compound is triethylamine trihydrofluoride, wherein the triethylamine trihydrofluoride compounds contain either $^{19}$F-fluorine or $^{18}$F-fluorine, provided that some of the triethylamine trihydrofluoride compounds used in the process contain $^{19}$F-fluorine and some of the triethylamine trihydrofluoride compounds used in the process contain $^{18}$F-fluorine. In aspects, the ratio of the $^{19}$F to $^{18}$F in the triethylamine trihydrofluoride compounds used in the process is at least 1000 to 1. In aspects, the only fluorine source used to fluorinate the carbocation of the organic compound is tetrabutylammonium fluoride, wherein the tetrabutylammonium fluoride compounds contain either $^{19}$F-fluorine or $^{18}$F-fluorine, provided that some of the tetrabutylammonium fluoride compounds used in the process contain $^{19}$F-fluorine and some of the tetrabutylammonium fluoride compounds used in the process contain $^{18}$F-fluorine. In aspects, the ratio of the $^{19}$F to $^{18}$F in the tetrabutylammonium fluoride compounds used in the process is at least 1000 to 1.

In embodiments, the organic compound can be any organic compound known in the art. In aspects, the organic compound comprises a saturated carbon atom. In aspects, the organic compound is capable of forming an electron rich carbocation when subjected to electrochemical oxidation. In aspects, the saturated carbon atom is the target for covalently bonding the fluorine to the organic compound. In aspects, the organic compound is capable of forming a carbocation that forms part of an aromatic ring when in neutral form. In aspects, the organic compound is capable of forming a carbocation that is adjacent to a carbonyl moiety. In aspects, the organic compound is capable of forming a carbocation that is adjacent to an amide moiety. In aspects, the organic compound is capable of forming a carbocation that is adjacent to an ester moiety. In aspects, the organic compound is capable of forming a carbocation that is adjacent to a sulfur atom. In aspects, the organic compound is capable of forming a carbocation that is adjacent to a sulfur moiety. In aspects, the organic compound is capable of forming a carbocation that is adjacent to a thioether moiety. In aspects, the organic compound comprises a substituted or unsubstituted aromatic ring and a substituted or unsubstituted heteroaromatic ring. In aspects, the organic compound comprises a substituted or unsubstituted aromatic ring. In aspects, the organic compound comprises a 4 to 8 membered aromatic ring. In aspects, the organic compound comprises a 5 or 6 membered aromatic ring. In aspects, the organic compound comprises a 5-membered aromatic ring. In aspects, the organic compound comprises a 6-membered aromatic ring. In aspects, the organic compound comprises a substituted or unsubstituted heteroaromatic ring. In aspects, the organic compound comprises a 4 to 8 membered heteroaromatic ring. In aspects, the organic compound comprises a 5 or 6 membered heteroaromatic ring. In aspects, the organic compound comprises a 5-membered heteroaromatic ring. In aspects, the organic compound comprises a 6-membered heteroaromatic ring. In aspects, the organic compound comprises a heteroaromatic ring, wherein the heteroatom is oxygen, sulfur, or nitrogen. In aspects, the organic compound comprises a 4 to 8 membered heteroaromatic ring, wherein the heteroatom is oxygen, sulfur, or nitrogen. In aspects, the organic compound comprises a 5 or 6 membered heteroaromatic ring, wherein the heteroatom is oxygen, sulfur, or nitrogen. In aspects, the organic compound comprises a 5-membered heteroaromatic ring, wherein the heteroatom is oxygen, sulfur, or nitrogen. In aspects, the organic compound comprises a 6-membered heteroaromatic ring, wherein the heteroatom is oxygen, sulfur, or nitrogen. In aspects, the organic compound comprises a heteroaromatic ring, wherein the heteroatom is oxygen. In aspects, the organic compound comprises a 4 to 8 membered heteroaromatic ring, wherein the heteroatom is oxygen. In aspects, the organic compound comprises a 5 or 6 membered heteroaromatic ring, wherein the heteroatom is oxygen. In aspects, the organic compound comprises a 5-membered heteroaromatic ring, wherein the heteroatom is oxygen. In aspects, the organic compound comprises a 6-membered heteroaromatic ring, wherein the heteroatom is oxygen. In aspects, the organic compound comprises a heteroaromatic ring, wherein the heteroatom is sulfur. In aspects, the organic compound comprises a 4 to 8 membered heteroaromatic ring, wherein the heteroatom is sulfur. In aspects, the organic compound comprises a 5 or 6 membered heteroaromatic ring, wherein the heteroatom is sulfur. In aspects, the organic compound comprises a 5-membered heteroaromatic ring, wherein the heteroatom is sulfur. In aspects, the organic compound comprises a 6-membered heteroaromatic ring, wherein the heteroatom is sulfur. In aspects, the organic compound comprises a heteroaromatic ring, wherein the heteroatom is nitrogen. In aspects, the organic compound comprises a 4 to 8 membered heteroaromatic ring, wherein the heteroatom is nitrogen. In aspects, the organic compound comprises a 5 or 6 membered heteroaromatic ring, wherein the heteroatom is nitrogen. In aspects, the organic compound comprises a 5-membered heteroaromatic ring, wherein the heteroatom is nitrogen. In aspects, the organic compound comprises a 6-membered heteroaromatic ring, wherein the heteroatom is nitrogen. In aspects, the organic compound comprises a phenyl group. In aspects, the organic compound comprises a benzyl group. In aspects, the aromatic group described herein is a substituted aromatic group, where the substituents may be as described herein. In aspects, the aromatic group described herein is an unsubstituted aromatic group. In aspects, the heteroaromatic group described herein is a substituted heteroaromatic group, where the substituents may be as described herein. In aspects, the heteroaromatic group described herein is an unsubstituted heteroaromatic group. In aspects, the organic compound is methyl(phenylthio)acetate, caffeine, methionine, or an NSAID (e.g., celecoxib).

In embodiments, the step of performing the electrochemical oxidation is conducted at a reduced temperature. In aspects, the reduced temperature is less than room temperature. In aspects, the reduced temperature is less than 25° C. In aspects, the reduced temperature is less than 20° C. In aspects, the reduced temperature is less than 15° C. In aspects, the reduced temperature is less than 10° C. In aspects, the reduced temperature is less than 5° C. In aspects, the reduced temperature is less than 0° C. In aspects, the reduced temperature is less than −5° C. In aspects, the reduced temperature is less than −10° C. In aspects, the reduced temperature is less than −15° C. In aspects, the reduced temperature is less than −20° C. In aspects, the reduced temperature is less than −25° C. In aspects, the reduced temperature is less than −30° C. In aspects, the reduced temperature is from about 10° C. to about −40° C. In aspects, the reduced temperature is from about 5° C. to about −40° C. In aspects, the reduced temperature is from about 0° C. to about −40° C. In aspects, the reduced temperature is from about 0° C. to about −30° C. In aspects, the reduced temperature is from about −5° C. to about −30° C. In aspects, the reduced temperature is from about −10° C. to about −30° C. In aspects, the reduced temperature is from about −15° C. to about −25° C. In aspects, the reduced temperature is about −10° C. In aspects, the reduced temperature is about −15° C. In aspects, the reduced temperature is about −20° C. In aspects, the reduced temperature is about −25° C. In aspects, the reduced temperature is about −30° C.

In embodiments, the step of performing the electrochemical oxidation is conducted at a reduced temperature and in the absence of an organic solvent that is capable of stabilizing a carbocation, in the absence of an acid this is capable of stabilizing a carbocation, and in the absence of a base that is capable of stabilizing a carbocation. The reduced temperature for this embodiment is the reduced temperatures described herein.

In embodiments, the fluorinated organic compound produced by the methods described herein is a positron emission tomography (PET) radioligand. The PET radioligand can be any compound that can be used in PET scan. A positron emission tomography is a method for medical imaging, capable of providing detailed functional information of physiological processes within the body, which has had a major impact in oncology due to its ability in disease detection, staging, response assessment therapy, and recurrent disease identification. The principle underlying PET systems is detecting the radiation range emitted from a radioactive substance administered into the human body. This PET radioligand contains radioisotopes of atoms (e.g., $^{18}$F-fluorine) in biological molecules (e.g., organic compounds) and, as such, has affinity for certain metabolic or biochemical processes, allowing the study of a particular function of the organ or assess the presence of disease revealed by excessive concentration of this substance at specific sites of the body. For example, $^{18}$F-FDG (glucose labeled with radioisotope of fluorine) is captured by cancer cells because these have a higher metabolism rate of glucose to normal cells. The molecules used in PET are labeled with positron emitting radioisotopes, which after wiped with atomic electrons emit two photons with energy of 511 keV in the same direction but in opposite directions. The PET systems detect and determine the spatial origin of photon pairs, the intersection of several lines of response generated by the tissue. Although the $^{18}$F-FDG is by far the tracer molecule most used in PET, new tracers are being developed for the diagnosis of cancer, hypoxia detection and angiogenesis, providing an expansion of the role of this modality in improving the clinical diagnosis.

Apparatus

In embodiments, the disclosure provide an electrolytic apparatus comprising the anode chamber which comprises the carbocationic organic compound and the fluorinated nucleophile. In aspects, the anode chamber further comprises an organic solvent, an acid, a base, or a combination of two or more thereof. In aspects, the electrolytic apparatus comprises a double electrochemical cell; wherein the anode chamber and the cathode chamber are separated by a cation exchange membrane. In aspects, the electrolytic apparatus comprises a double electrochemical cell; wherein the anode chamber and the cathode chamber are separated by an anion exchange membrane. In aspects, the electrolytic apparatus comprises a multi-chamber electrochemical cell; and wherein the anode chamber and the cathode chamber are separated by a cation exchange membrane. In aspects, the electrolytic apparatus comprises a multi-chamber electrochemical cell; and wherein the anode chamber and the cathode chamber are separated by an anion exchange membrane.

EMBODIMENTS 1-40

Embodiment 1. A method of producing a fluorinated organic compound, the method comprising the steps of: (i) performing electrochemical oxidation on the organic compound, thereby forming a carbocation; and (ii) adding a fluorinated nucleophile to the carbocation, thereby forming the fluorinated organic compound Embodiment 2. The method of Embodiment 1, comprising performing electrochemical oxidation at a reduced temperature.

Embodiment 3. The method of Embodiment 2, wherein the reduced temperature is less than 0° C.

Embodiment 4. The method of Embodiment 2, wherein the reduced temperature is less than −15° C.

Embodiment 5. The method of any one of Embodiments 1 to 4, comprising performing electrochemical oxidation in a mixture comprising the organic compound and (i) an organic solvent, (ii) an acid and a base, (iii) an acid, or (iv) a base.

Embodiment 6. The method of Embodiment 5, wherein the organic solvent comprises trifluoroethanol; and wherein the acid comprises trifluoromethanesulfonic acid.

Embodiment 7. The method of Embodiment 5 or 6, wherein the organic solvent, the acid, or the base is present in an amount effective to stabilize the carbocation.

Embodiment 8. The method of any one of Embodiments 1 to 7, comprising adding the fluorinated nucleophile to a mixture comprising the organic compound and (i) an organic solvent, (ii) an acid and a base, (iii) an acid, or (iv) a base.

Embodiment 9. The method of any one of Embodiments 1 to 8, further comprising the step of discontinuing electrochemical oxidation prior to adding the fluorinated nucleophile to the carbocation.

Embodiment 10. The method of any one of Embodiments 1 to 9, wherein the organic compound has a saturated carbon atom.

Embodiment 11. The method of any one of Embodiments 1 to 9, wherein the organic compound comprises an aromatic ring or a heteroaromatic ring.

Embodiment 12. The method of one of Embodiments 1 to 9, wherein the organic compound is methyl(phenylthio)acetate.

Embodiment 13. The method of one of Embodiments 1 to 12, wherein a saturated carbon atom is a target for covalently bonding the fluorine to the organic compound.

Embodiment 14. The method of any one of Embodiments 1 to 13, wherein the fluorinated nucleophile does not comprise a thiofluorine group.

Embodiment 15. The method of any one of Embodiments 1 to 14, wherein the fluorinated nucleophile is a mixture of two or more compounds selected from $K(^{18}F)F—K_{222}$, cesium fluoride, potassium fluoride, triethylamine trihydrofluoride, and tetrabutylammonium fluoride.

Embodiment 16. The method of any one of Embodiments 1 to 14, wherein the fluorinated nucleophile is $K(^{18}F)F—K_{222}$.

Embodiment 17. The method of any one of Embodiments 1 to 14, wherein the fluorinated nucleophile is cesium fluoride.

Embodiment 18. The method of any one of Embodiments 1 to 14, wherein the fluorinated nucleophile is potassium fluoride.

Embodiment 19. The method of any one of Embodiments 1 to 14, wherein the fluorinated nucleophile is triethylamine trihydrofluoride.

Embodiment 20. The method of any one of Embodiments 1 to 14, wherein the fluorinated nucleophile is tetrabutylammonium fluoride.

Embodiment 21. The method of any one of Embodiments 1 to 20, wherein the fluorinated nucleophile is a radio-fluorinated nucleophile.

Embodiment 22. The method of Embodiment 21, wherein the radio-fluorinated nucleophile comprises $^{18}F$-fluoride.

Embodiment 23. The method of Embodiment 21 or 22, wherein the fluorinated nucleophile is a no-carrier added radioactive fluorinated nucleophile.

Embodiment 24. The method of any one of Embodiments 1 to 23, wherein the fluorinated organic compound is a radio-fluorinated organic compound.

Embodiment 25. The method of any one of Embodiments 1 to 24, wherein the method for producing a fluorinated organic compound is a method of covalently bonding at least one fluorine to a carbocation.

Embodiment 26. The method of any one of Embodiments 1 to 25, wherein the fluorinated compound is a positron emission tomography radioligand.

Embodiment 27. The method of any one of Embodiments 1 to 26, wherein the method of producing the fluorinated organic compound is performed by electrochemical oxidation in a double electrochemical cell or a multi-chamber electrochemical cell; wherein the electrochemical cell comprises an anodic cell and a cathodic cell separated by a cation exchange membrane or an anion exchange membrane.

Embodiment 28. The method of any one of Embodiments 1 to 27, wherein the method of producing the fluorinated organic compound is performed in a flow-through platform.

Embodiment 29. The method of any one of Embodiments 1 to 27, wherein the method of producing the fluorinated organic compound is performed in a microfluidic platform.

Embodiment 30. The method of any one of Embodiments 1 to 29, wherein the electrochemical oxidation is cation pool formation.

Embodiment 31. A fluorinated compound produced by the method of any one of Embodiments 1 to 30.

Embodiment 32. A positron emission tomography radioligand produced by the method of any one of Embodiments 1 to 30.

Embodiment 33. An electrolytic apparatus comprising a cathode chamber, an anode chamber, a carbocation, and a fluorinated nucleophile.

Embodiment 34. The apparatus of Embodiment 33, wherein the anode chamber comprises the carbocation and the fluorinated nucleophile Embodiment 35. The apparatus of Embodiment 33 or 34, wherein the anode chamber further comprises (i) an organic solvent, (ii) an acid and a base, (iii) an acid, or (iv) a base.

Embodiment 36. The apparatus of any one of Embodiments 33 to 35, wherein the electrolytic apparatus comprises a double electrochemical cell; and wherein the anode chamber and the cathode chamber are separated by a cation exchange membrane or an anion exchange membrane.

Embodiment 37. The apparatus of any one of Embodiments 33 to 35, wherein the electrolytic apparatus comprises a multi-chamber electrochemical cell; and wherein the anode chamber and the cathode chamber are separated by a cation exchange membrane or an anion exchange membrane.

Embodiment 38. The apparatus of any one of Embodiments 33 to 37, wherein the anode chamber and the cathode chamber are separated by a cation exchange membrane.

Embodiment 39. The apparatus of any one of Embodiments 33 to 37, wherein the anode chamber and the cathode chamber are separated by an anion exchange membrane.

Embodiment 40. The method of any one of Embodiments 1 to 30 performed in the apparatus of any one of Embodiments 33 to 39.

EMBODIMENTS A1-A50

Embodiment A1. A method of producing a fluorinated organic compound, the method comprising the steps of: (i) performing electrochemical oxidation on the organic compound, thereby forming a carbocation within the organic compound; (ii) adding a fluorinated nucleophile to the carbocation, thereby forming the fluorinated organic compound. The step of adding a fluorinated nucleophile to the carbocation may alternatively be referred to as contacting a fluorinated nucleophile with the carbocation.

Embodiment A2. The method of Embodiment A1, comprising performing electrochemical oxidation at a reduced temperature.

Embodiment A3. The method of Embodiment A2, wherein the reduced temperature is less than 0° C.

Embodiment A4. The method of Embodiment A3, wherein the reduced temperature is less than −15° C.

Embodiment A5. The method of any one of Embodiments A1 to A4, wherein (i) comprises performing electrochemical oxidation in a liquid medium which comprises a mixture comprising: (a) the organic compound and an organic solvent; (b) the organic compound, an organic solvent, and an acid; (c) the organic compound, an organic solvent, and a base; (d) the organic compound, an acid, and a base; or (e) the organic compound, an organic solvent, an acid, and a base.

Embodiment A6. The method of Embodiment A5, wherein the organic solvent, the acid, and the base are present in an amount effective to stabilize the carbocation within the organic compound.

Embodiment A7. The method of Embodiment A5 or A6, wherein performing electrochemical oxidation comprises performing electrochemical oxidation in the liquid medium which comprises the mixture comprising the organic compound, the organic solvent, and the acid.

Embodiment A8. The method of Embodiment A7, wherein the molar ratio of the organic solvent to the acid is from about 0.8:1 to about 3:1.

Embodiment A9. The method of Embodiment A8, wherein the molar ratio of the organic solvent to the acid is from about 0.8:1 to about 1.3:1.

Embodiment A10. The method of any one of Embodiments A5 to A9, wherein: (i) the organic solvent is trifluoroethanol, hexafluoroisopropanol, or a combination thereof; (ii) the acid is trifluoromethanesulfonic acid, tetrabutylammonium perchlorate, tetrabutylammonium tetrafluoroborate, trifluoroacetic acid, p-toluenesulfonic acid, or a combination thereof; and (iii) the base is a conjugate base of trifluoromethanesulfonic acid, a conjugate base of tetrabutylammonium perchlorate, a conjugate base of tetrabutylammonium tetrafluoroborate, trifluoroacetic acid, a conjugate base of p-toluenesulfonic acid, or a combination thereof.

Embodiment A11. The method of Embodiment A10, wherein the organic solvent comprises trifluoroethanol, and the acid comprises trifluoromethanesulfonic acid.

Embodiment A12. The method of Embodiment A11, wherein the acid further comprises tetrabutylammonium perchlorate.

Embodiment A13. The method of Embodiment A5 or A6, wherein performing electrochemical oxidation comprises performing electrochemical oxidation in a liquid medium which comprises a mixture comprising the organic compound, the acid, and the base.

Embodiment A14. The method of Embodiment A13, wherein: (i) the acid is trifluoromethanesulfonic acid and the base is the conjugate base of trifluoromethanesulfonic acid; (ii) the acid is tetrabutylammonium perchlorate and the base is the conjugate base of tetrabutylammonium perchlorate; (iii) the acid is tetrabutylammonium tetrafluoroborate and the base is the conjugate base of tetrabutylammonium tetrafluoroborate; (iv) the acid is trifluoroacetic acid and the base is the conjugate base of trifluoroacetic acid; or (v) the acid is p-toluenesulfonic acid and the base is the conjugate base of p-toluenesulfonic acid.

Embodiment A15. The method of any one of Embodiments A5 to A14, wherein adding the fluorinated nucleophile to the carbocation comprises adding the fluorinated nucleophile to the mixture of (a), (b), (c), (d), or (e).

Embodiment A16. The method of any one of Embodiments A1 to A15, further comprising the step of discontinuing electrochemical oxidation prior to adding the fluorinated nucleophile to the carbocation.

Embodiment A17. The method of any one of Embodiments A1 to A16, wherein the organic compound comprises a saturated carbon atom.

Embodiment A18. The method of any one of Embodiments A1 to A17, wherein the carbocation is an electron rich carbocation.

Embodiment A19. The method of any one of Embodiments A1 to A18, wherein the carbocation is within a substituted or unsubstituted aromatic ring or a substituted or unsubstituted heteroaromatic ring.

Embodiment A20. The method of any one of Embodiments A1 to A18, wherein the carbocation forms part of a substituted or unsubstituted aromatic or heteroaromatic ring when in neutral form or is adjacent to a carbonyl moiety, an amide moiety, an ester moiety, a sulfur atom, or a thioether moiety.

Embodiment A21. The method of any one of Embodiments A1 to A20, wherein the organic compound is methyl (phenylthio)acetate, caffeine, methionine, or celecoxib.

Embodiment A22. The method of any one of Embodiments A1 to A21, wherein the fluorinated nucleophile does not comprise a thiofluorine group.

Embodiment A23. The method of any one of Embodiments A1 to A22, wherein the fluorinated nucleophile comprises $K(^{18}F)F$—$K_{222}$, cesium fluoride, potassium fluoride, triethylamine trihydrofluoride, or tetrabutylammonium fluoride.

Embodiment A24. The method of any one of Embodiments to A25, wherein the fluorinated nucleophile comprises a mixture of two or more compounds selected from the group consisting of $K(^{18}F)F$—$K_{222}$, cesium fluoride, potassium fluoride, triethylamine trihydrofluoride, and tetrabutylammonium fluoride.

Embodiment A25. The method of any one of Embodiments A1 to A24, wherein the fluorinated nucleophile is a radiofluorinated nucleophile.

Embodiment A26. The method of Embodiment A25, wherein the radiofluorinated nucleophile comprises $^{18}F$-fluorine.

Embodiment A27. The method of Embodiment A26, wherein the $^{18}F$-fluorine has an activity of at least 1 curie per millimole.

Embodiment A28. The method of Embodiment A26 or A27, wherein the ratio of $^{19}F$-fluorine to $^{18}F$-fluorine in the fluorinated organic compound is at least 1000 to 1.

Embodiment A29. The method of any one of Embodiments A1 to A28, wherein the fluorinated nucleophile is a no-carrier added fluorinated nucleophile.

Embodiment A30. The method of Embodiment A29, wherein the fluorinated organic compound is a radiofluorinated organic compound.

Embodiment A31. The method of any one of Embodiments A1 to A30, wherein the fluorinated organic compound is a positron emission tomography radioligand.

Embodiment A32. The method of any one of Embodiments A1 to A31, wherein the method of producing the fluorinated organic compound is performed by electrochemical oxidation in a double electrochemical cell or a multi-chamber electrochemical cell; wherein the electrochemical cell comprises an anodic cell and a cathodic cell separated by a cation exchange membrane or an anion exchange membrane.

Embodiment A33. The method of any one of Embodiments A1 to A32, wherein the method of producing the fluorinated organic compound is performed in a flow-through platform.

Embodiment A34. The method of any one of Embodiments A1 to A32, wherein the method of producing the fluorinated organic compound is performed in a microfluidic platform.

Embodiment A35. The method of any one of Embodiments A1 to A34, wherein the electrochemical oxidation forms a cation pool.

Embodiment A36. A fluorinated organic compound produced by the method of any one of Embodiments A1 to A35.

Embodiment A37. A positron emission tomography radioligand produced by the method of any one of Embodiments A1 to A35.

Embodiment A38. An electrolytic apparatus comprising a cathode chamber, an anode chamber, a carbocation within an organic compound, and a fluorinated nucleophile.

Embodiment A39. The apparatus of Embodiment A39, wherein the anode chamber comprises the carbocation within the organic compound and the fluorinated nucleophile.

Embodiment A40. The apparatus of Embodiment A38 or A39, wherein the anode chamber further comprises an organic solvent, an acid, a base, or a combination of two or more thereof.

Embodiment A41. The apparatus of any one of Embodiments A38 to A40, wherein the electrolytic apparatus comprises a double electrochemical cell; and wherein the anode chamber and the cathode chamber are separated by a cation exchange membrane or an anion exchange membrane.

Embodiment A42. The apparatus of any one of Embodiments A38 to A40, wherein the electrolytic apparatus comprises a multi-chamber electrochemical cell; and wherein the anode chamber and the cathode chamber are separated by a cation exchange membrane or an anion exchange membrane.

Embodiment A43. The apparatus of any one of Embodiments A38 to A42, wherein the anode chamber and the cathode chamber are separated by a cation exchange membrane.

Embodiment A44. The apparatus of any one of Embodiments A38 to A42, wherein the anode chamber and the cathode chamber are separated by an anion exchange membrane.

Embodiment A45. The method of any one of Embodiments A1 to A35 performed in the apparatus of any one of Embodiments A38 to A44.

EXAMPLES

Example 1: Electrochemical Flash Fluorination and Radiofluorination

A new method for rapid late-stage fluorination using the cation pool technique is presented. Fluorination and no-carrier-added radio-fluorination of methyl(phenylthiol)acetate was performed. The carbocations formed by electrochemical oxidation were stabilized using a divided electrochemical cell and 2-2-2-trifluoroethanol (TFE) as solvent at low temperatures. At the end of electrolysis, either stable isotope $^{19}$F-fluoride or, no-carrier-added radioactive $^{18}$F-fluoride were added to the reaction mixture to form the fluorinated or radio-fluorinated product.

Here, for the first time, the electrochemical fluorination and radio-fluorination of organic molecules using the cation pool technique is reported, where the fluoride ions are added post electrolysis. This approach enables the use of the cation pool method for the widely useful application of rapid and late-stage fluorination and radiochemistry. The cation pool method has tremendous potential especially for radiofluorination experiments. The excess concentration of reactive cations can provide an efficient reaction mechanism for fluorination under low fluoride concentrations encountered during radiofluorination. Furthermore, radiochemical yield, which is reduced by decay of the radioisotope, can benefit from a rapid late-stage fluorination reaction. The cation pool can be prepared prior to cyclotron production of $^{18}$F isotope, thereby, providing a truly late-stage fluorination reaction, maximizing radiochemical yield by minimizing decay through a flash reaction of the previously prepared cations with $^{18}$F-fluoride.

In this study, a divided electrochemical cell was used for electrolysis. The anodic and cathodic chambers were separated by a nafion membrane. Methyl(phenylthiol)acetate (12 mM) was used as substrate and 2,2,2-trifluoroethanol (TFE) as solvent with different supporting electrolytes in the anodic chamber. TFE, tetrabutylammonium perchlorate (TBAP) and triflic acid were used in the cathodic chamber. Previous reports on electrochemical fluorination of methyl (phenylthiol)acetate and the importance of fluorinated thioethers in pharmaceuticals guided our choice for the substrate. Balandeh et al, Electrochem. Soc., 2017, 164, G99-G103; Leroux et al, Chem. Rev., 2005, 105, 827-856. Traditional fluorination of sulfoxides have been based on fluoro-Pummerer rearrangement with DAST, electrophilic fluorination of thioethers and the combinations of chemical oxidants with nucleophilic fluorinating reagents (see reference 25). Previous electrochemical fluorination of thioethers were performed with excess amounts of HF salts or TBAF present in the cell during electrolysis, resulting in low fluoride conversion yield and preventing no-carrier-added fluorination. Here, electrochemical oxidation was performed for 60 min at a constant potential of 1.6 V vs Ag wire quasi-reference electrode followed by addition of a fluoride nucleophile to the anodic chamber at the end of electrochemical oxidation. The mixture was stirred and allowed to react for 30 min while the temperature was rising to room temperature. With 168 mM of CsF, KF, triethylammonium fluoride ($Et_3N_3HF$) and tetrabutylammonium fluoride (TBAF) used as fluoride (nucleophile) sources, respective yields of 4.5%, 1.4%, 4% and 4.5% of methyl 2-fluoro-2-(phenothio) acetate were obtained. The yields were quantified using gas chromatography mass spectrometry (GC-MS). FIG. 1 shows the schematic of the reaction and representative GC-MS chromatograms can be found in the supporting information. Electrolysis was repeated with TBAF at different temperatures of 21° C., 0° C., −20° C. and −40° C. and chemical yields of 2.2%, 4%, 6% and 3% were obtained respectively. The drop in the yield from −20° C. to −40° C. is due to the low oxidation current resulting in the slowing of precursor oxidation. 68% of the precursor was consumed when oxidation was performed at −20° C., while only 12% of the precursor was consumed at −40° C. −20° C. was chosen as the optimum temperature for further optimization. The effect of changes in supporting electrolyte on the chemical yield is shown in Table 1. It can be seen from Table 1 that TBAP alone results in negligible product formation, while addition of 14.2 mM of triflic acid increases the yield to 6%. The highest yield of 12.5% was obtained where only 142 mM of triflic acid was used without addition of salts as supporting electrolyte. Further optimization was performed using only triflic acid as supporting electrolyte and the effect of triflic acid concentration on the yield was examined. Yields of 3.6%, 12.5% and 0% was obtained when 71 mM, 142 mM and 284 mM of triflic acid were used, respectively. The effect of precursor concentration on the product yield is presented in table 2. Precursor concentration changes from 0.5 mM to 24 mM resulted in only a moderate change in the yield.

TABLE 1

Effect of supporting electrolyte on the chemical yield of 2. Electrolysis was carried out using 12 mM of 1 in TFE for 60 min at 1.6 V vs Ag wire at −20° C. followed by addition of 168 mM of TBAF post electrolysis.

| Supporting electrolyte | Yield (%) |
| --- | --- |
| 50 mM Tetrabutylammonium perchlorate (TBAP) | 0 |
| 300 mM Tetrabutyl ammonium perchlorate (TBAP) | 0 |
| 300 mM Tetrabutyl ammonium perchlorate + 14.2 mM triflic acid | 6.0 |
| 300 mM Tetrabutylammonium tetrafluoroborate + 14.2 mM triflic acid | 1.3 |
| 300 mM p-Toluenesulfonic acid + 14.2 mM triflic acid | 2.0 |
| 142 mM triflic acid | 12.5 |

TABLE 2

Effect of precursor 1 concentration on the chemical yield of product 2. Electrolysis was carried out using precursor 1, and 142 mM of triflic acid in TFE for 60 min at 1.6 V vs Ag wire at −20° C. 168 mM TBAF was added at the of electrochemical oxidation.

| Precursor concentration (mM) | Yield (%) (n = 3) |
| --- | --- |
| 0.5 | 8.5 ± 0.9 |
| 1 | 9.6 ± 1.0 |
| 2 | 11.5 ± 1.2 |
| 4 | 10.6 ± 1.1 |
| 6 | 12.7 ± 1.4 |
| 12 | 11.2 ± 1.3 |
| 24 | 9.2 ± 1.0 |

Due to the diminishing [$^{18}$F]-TBAF concentration during no-carrier-added radiochemistry experiments, the effect of lowering of TBAF concentration and ratio of TBAF to triflic acid concentration were also investigated and the results are shown in Table 3. It was observed that by lowering the TBAF concentration the product yield decreased to 1.5% when 21 mM of TBAF was used. It was further observed that the ratio of TBAF to triflic acid concentration plays a crucial role with optimum product yield obtained when his ratio is maintained at 1.18. This may be due to the instability of product at low pH where TBAF addition can act as a base to increase the pH of the solution.

TABLE 3

Effect of TBAF concentration and TBAF concentration/triflic acid concentration ratio on the chemical yield of product 2. Electrolysis was carried out using 12 mM of 1 and triflic acid in TFE for 60 min at 1.6 V vs Ag wire at −20° C. The values marked with an asterisk in the second column reflect experiments where triflic acid concentration was kept constant at 142 mM.

| TBAF concentration (mM) | TBAF concentration/Triflic acid concentration | Yield (%) |
| --- | --- | --- |
| 21 | 1.18 | 1.6 |
|  | 0.15 | 0 |
| 42 | 1.18 | 3.8 |
|  | 0.30 | 0 |
| 84 | 1.18 | 4.0 |
|  | 0.60 | 0 |
| 168 | 1.18 | 12.5 |
|  | 2.36 | 3.6 |

Using the optimized parameters, radio-fluorination of 1 was performed with the cation pool method with 142 mM of triflic acid and 24 mM of 1 in TFE in the anodic chamber. Radiochemical fluorination efficiencies (RCFEs) were calculated based on conversion of [$^{18}$F]-fluoride. Initially [$^{18}$F]-fluoride in the form of [$^{18}$F]-TBAF was added to the anodic chamber after 60 min of electrolysis, however no radio-fluorinated product was observed. Due to the diminishing TBAF concentrations in the radiochemistry experiment, addition of a non-nucleophilic base was necessary to increase the pH to 3, at which point the product was observed to be stable. To address this challenge, 5 mCi of [$^{18}$F]-fluoride was mixed with 300 mM of 2,6-di-tert-butyl-4-methylpyridine and the mixture was added to the anodic chamber after electrolysis resulting in RCFE of 5.7±1.0% (n=3) and molar activity of 75±11 mCi/μM (n=3). Similar to cold experiments with [$^{19}$F]-TBAF, samples for characterization were taken 30 min after [$^{18}$F]-fluoride addition. Notably, RCFE of 4.8±0.6% (n=3) was obtained after just 5 min post [$^{18}$F]-fluoride addition.

This example demonstrates a new and useful tool for rapid late-stage fluorination and radio-fluorination using the cation pool method. This is made possible through generation and pooling of stable cations under low temperature using TFE as solvent, and the subsequent fluorination reaction of carbocations with fluoride under non-oxidative conditions. Cation pool fluorination prevents further oxidation of the fluorinated product during the electrolysis and rapid late-stage radio-fluorination with this method can minimize the losses of $^{18}$F-fluoride due to radioactive decay. More in-depth studies of scope and the use of microfluidic platforms are currently in progress. Flash fluorination and radiofluorination based on the cation pool method can be used to produce PET radioligands and fluorinated pharmaceuticals, expanding the library of fluorinated bioactive molecules available for medicinal chemistry and molecular imaging.

Supporting Information for Example 1

Materials. 2,2,2-trifluoroethanol (TFE, 99.9%, $C_2H_3F_3O$), trifluoromethanesulfonic acid (triflic acid, $CF_3SO_3H$, 99%) and methyl(phenylthio)acetate ($C_9H_{10}O_2S$, 99%) were purchased from Oakwood Chemical. Acetonitrile (ACN, anhydrous, 98%), tetrabutylammonium fluoride solution 1.0 M in THF (TBAF solution, ~5 wt % water), cesium fluoride (99%, CsF), Potassium fluoride (≥99.9%, KF), triethylamine trihydrofluoride (98%, $(C_2H_5)_3N·3HF$) and platinum wire (99.9%) were purchased from Sigma-Aldrich. Tetrabutylammonium perchlorate (TBAP, >98.0%, $C_{16}H_{36}ClNO_4$), tetrabutylammonium tetrafluoroborate (>98.0%, $C_{16}H_{36}BF_4N$) and p-toluenesulfonic acid (>98.0%, $C_7H_8O_3S·H_2O$) were purchased from TCI America. 2,6-Di-Tert-butyl-4-methylpyridine (98%, $C_{14}H_{23}N$) was purchased from Ark Pharm, Inc. Nafion® membrane N117, 7 mils (178 μm thickness) was purchased from Fuel Cell Earth. Analytical grade (AG) MP-1M anion exchange resin was purchased from Bio-Rad.

Figure 2:
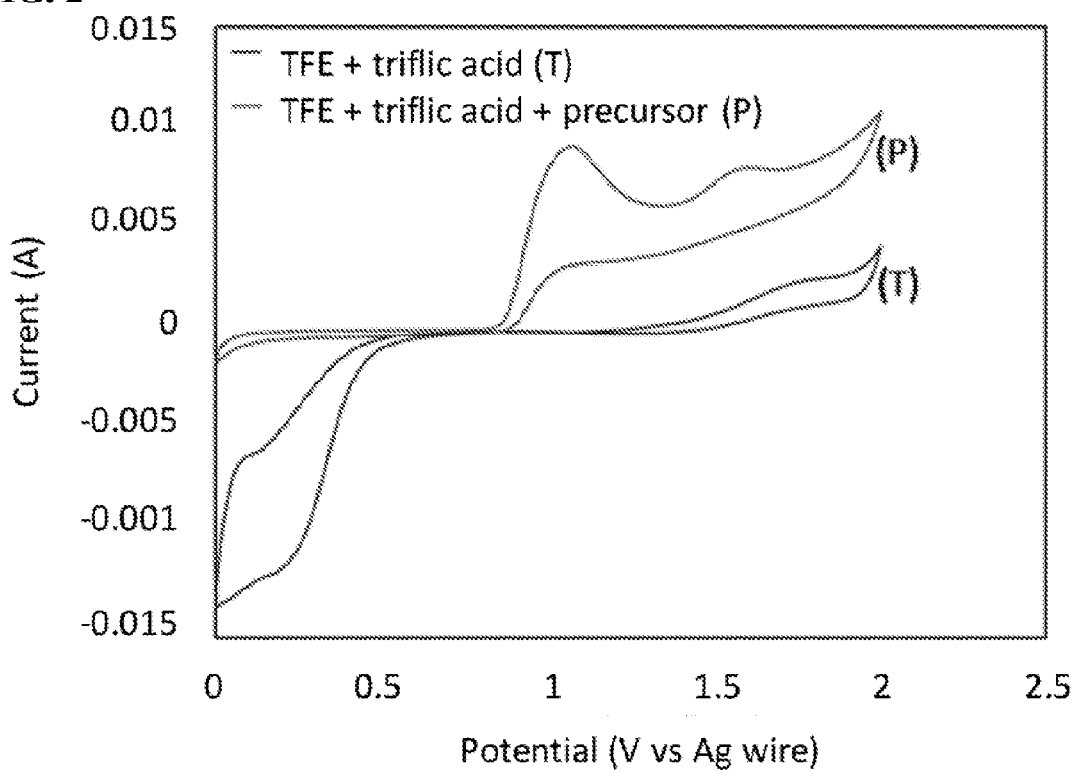
FIG. 2 shows CVs of TFE and triflic acid (also known as trifluoromethanesulfonic acid) with and without precursor (background). The CVs were run with 200 mv·s$^{-1}$ scan rate at room temperature (21° C.) using a divided cell and no stirring.

Electrochemical synthesis. The electrochemical oxidation (the cation pool formation) and cyclic voltammetry (CV) were performed using an H shape divided 3-electrode cell with two platinum wires (length=200 mm, diameter=0.33 mm) as working and counter electrodes and Ag wire as quasi-reference electrode. The cathodic chamber and anodic chamber were separated by a nafion membrane. The anodic chamber contained 10 ml of TFE as solvent, methyl(phenylthio)acetate (precursor) and different supporting electrolytes such as triflic acid, tetrabutylammonium perchlorate, tetrabutylammonium tetrafluoroborate and p-toluenesulfonic acid. The cathodic chamber contained 10 ml of TFE as solvent, 300 mM tetrabutylammonium perchlorate and 757 mM of triflic acid. The reference electrode (Ag wire) was immersed in the anodic reaction mixture. The counter electrode and working electrode were cleaned before each experiment using potential cycling in 1 M sulfuric acid solution in water. The electrodes were cycled between −2 V and 2 V (2 electrode configuration) 10 times before each experiment. The electrochemical oxidation of methyl(phenylthio)acetate (carbocations formation) was performed at constant potential of 1.6 V vs Ag wire for 60 min. At the end of electrolysis, the nucleophile (TBAF) was added to the anodic chamber and allowed to react for 30 min while the reaction mixture was stirred using a magnetic stirring bar at 500 RPM and temperature was rising to the room temperature. The CVs and electrochemical oxidation experiments were performed using the Metrohm PGSTAT128N electrochemical workstation. The CVs were performed using a 200 mV/s scan rate and no stirring. FIG. 2 shows the CV of background (TFE+supporting electrolyte in the anodic chamber) and CV of the cation pool reaction mixture (methyl(phenylthio)acetate+TFE+supporting electrolyte in the anodic chamber). It can be seen from FIG. 1 that the oxidation of precursor starts at 0.9 V vs Ag wire and reaches a peak at 1.08 V vs Ag wire due to the diffusion limit. The CV of the background shows very small anodic currents up to 1.5 V vs Ag wire; by increasing the potential further the background anodic current starts to increase to higher values. It also can be seen that adding the precursor to the solution can suppress the cathodic currents at potentials lower than 0.5 V vs Ag wire.

Characterization. Gas chromatography-mass spectrometry (GC-MS). The product identification and quantification was performed using GC-MS. Mass spectra and chromatograms were carried out using an Agilent 5975C Triple-Axis Detector (TAD) inert MSD mass spectrometer coupled with an Agilent 7890A gas chromatograph. The mass spectrum was set to electron ionization mode with a voltage of 1.9 kV. The mass range was 50-250 (amu). The details of gas chromatograph's column and the method are outlined below:

Inlet was set at 120° C. and had 1:10 split ratio. Oven was set to 120° C. and held for 1 min, then increased to 138° C. at a rate of 1° C./min and held for 15 minutes.

Column was Agilent 122-5532, maximum operating temperature 325° C.; 30 m length, 250 μm internal diameter and 0.25 μm film thickness. A constant flow of 1 mL/min was delivered to the transfer column. The transfer column Agilent G3185-60062, 450° C.; 0.17 m length, 100 μm internal diameter and 0 μm film thickness delivered a constant flow of 1.5 mL/min to the source. The GC-MS method had a 10 min solvent delay in order to enhance the MS filament lifetime.

Figure 3:
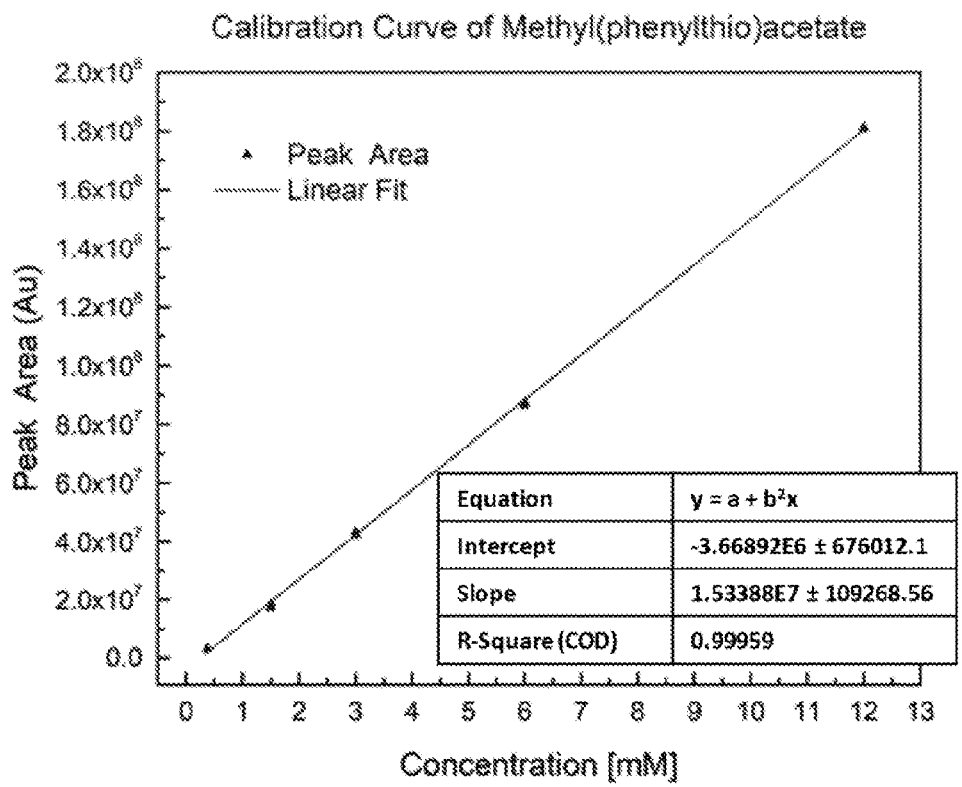
FIG. 3 shows the GC calibration plot used in the quantification of formation of product 2.
Figure 4:
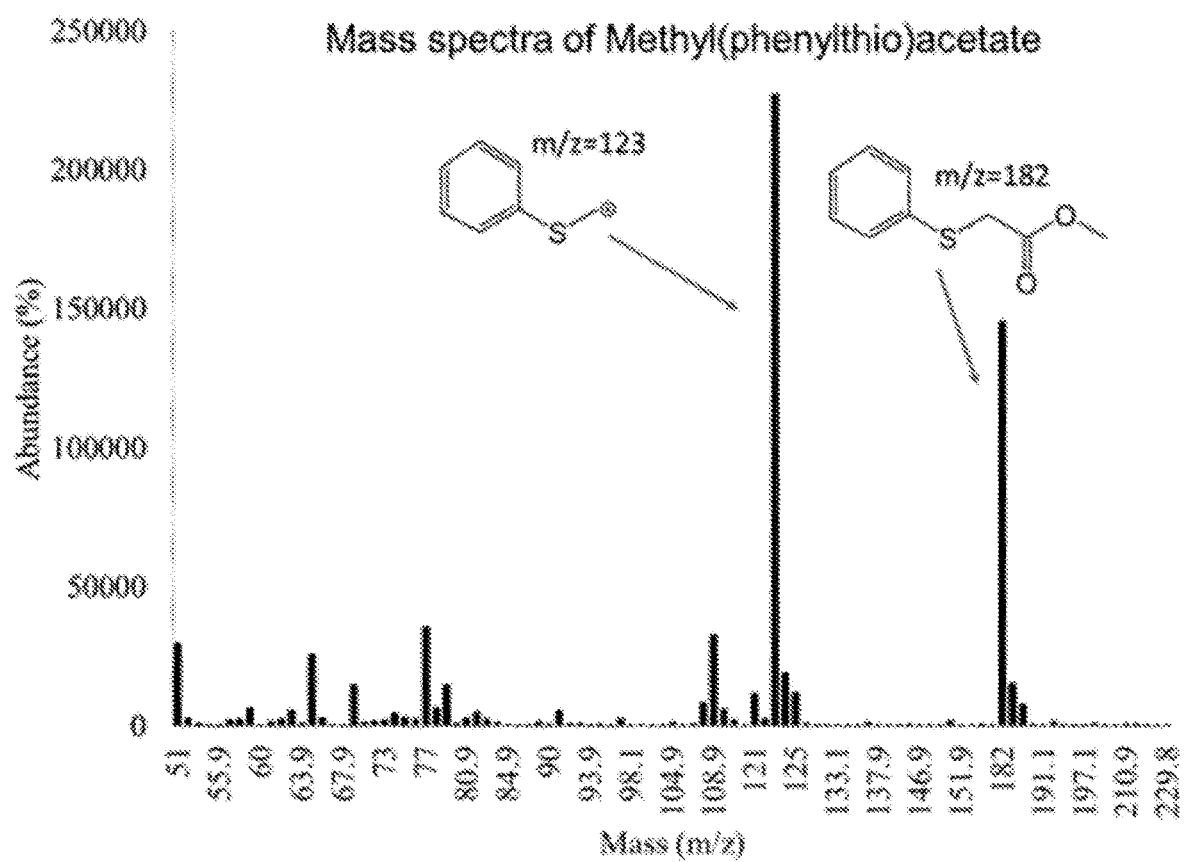
FIG. 4 shows the mass spectrum of the pure precursor 1.
Figure 5:
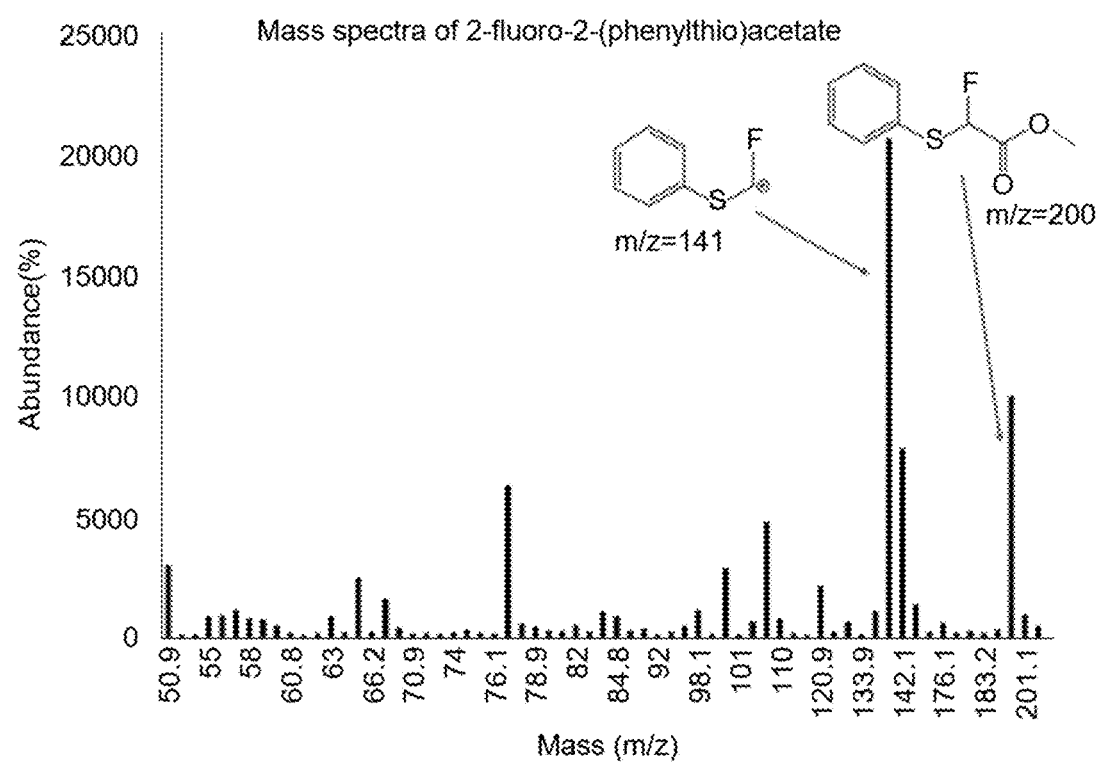
FIG. 5 shows the mass spectrum of the product 2.
Figure 6:
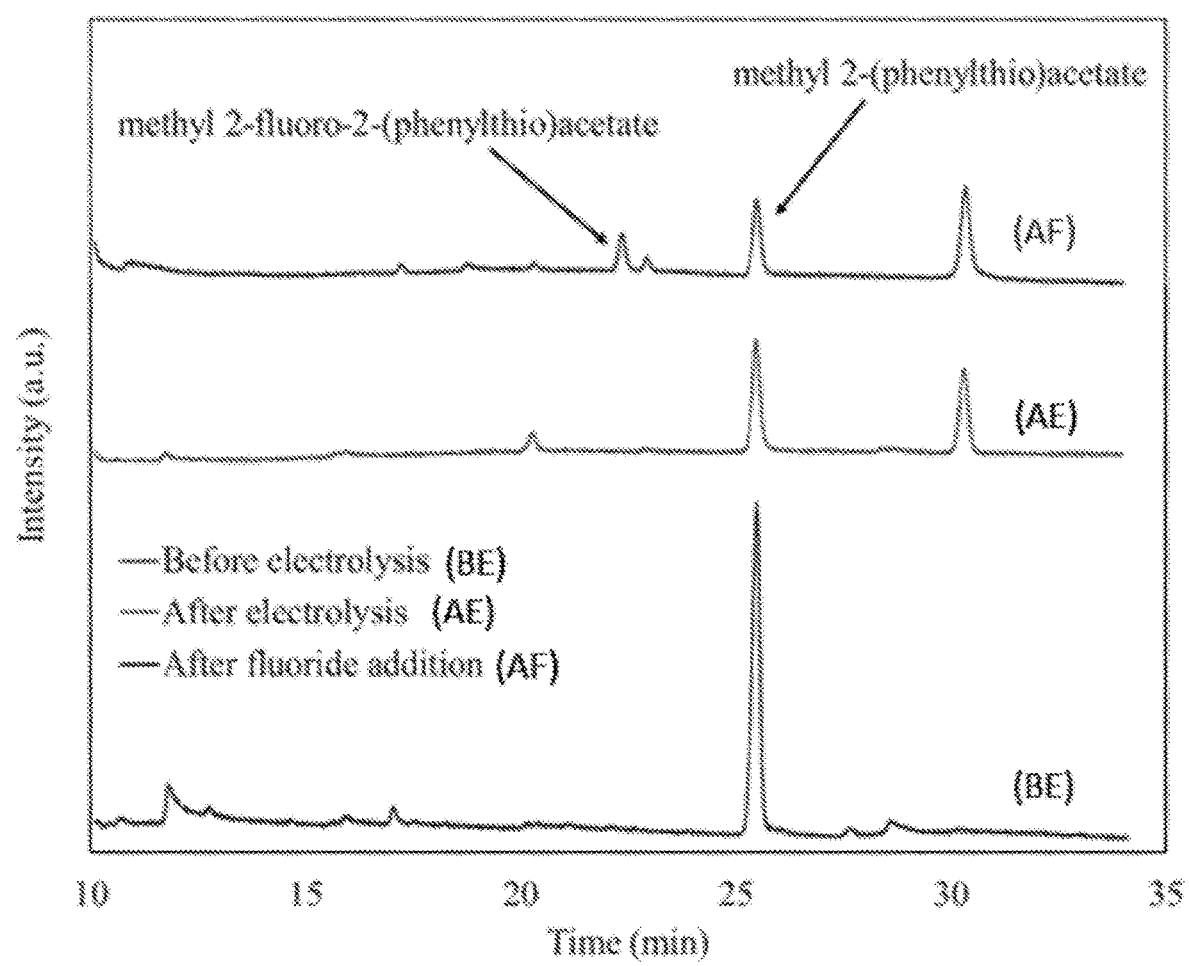
FIG. 6 shows GC-MS chromatograms of the crude reaction mixture before and after electrochemical oxidation and after fluoride addition. Electrolysis was carried out using 12 mM of 1 and 142 mM of triflic acid in TFE (also known as trifluoroethanol, e.g., 2,2,2-trifluoroethanol) for 60 min at 1.6 V vs Ag wire at −20° C. 168 mM TBAF (also known as tetra-n-butylammonium fluoride) was added at the end of electrochemical oxidation and allowed to react for 30 min while the reaction mixture was stirring and temperature was rising to the room temperature.

FIG. 3 is the GC-MS calibration plot used in the quantification of product 2 yield. FIGS. 4 and 5 show the GC-MS mass spectrum of the precursor and product, respectively. FIG. 6 shows a representative GC-MS chromatogram of the crude product. It can be seen from FIG. 6 that after electrolysis, 70% of the precursor has been consumed and no product peak can be observed at 21.7 min. The product is only observed after the injection of TBAF post electrolysis, pointing to the reaction of fluoride anions with stabilized carbocations formed during electrolysis.

Figure 7A:
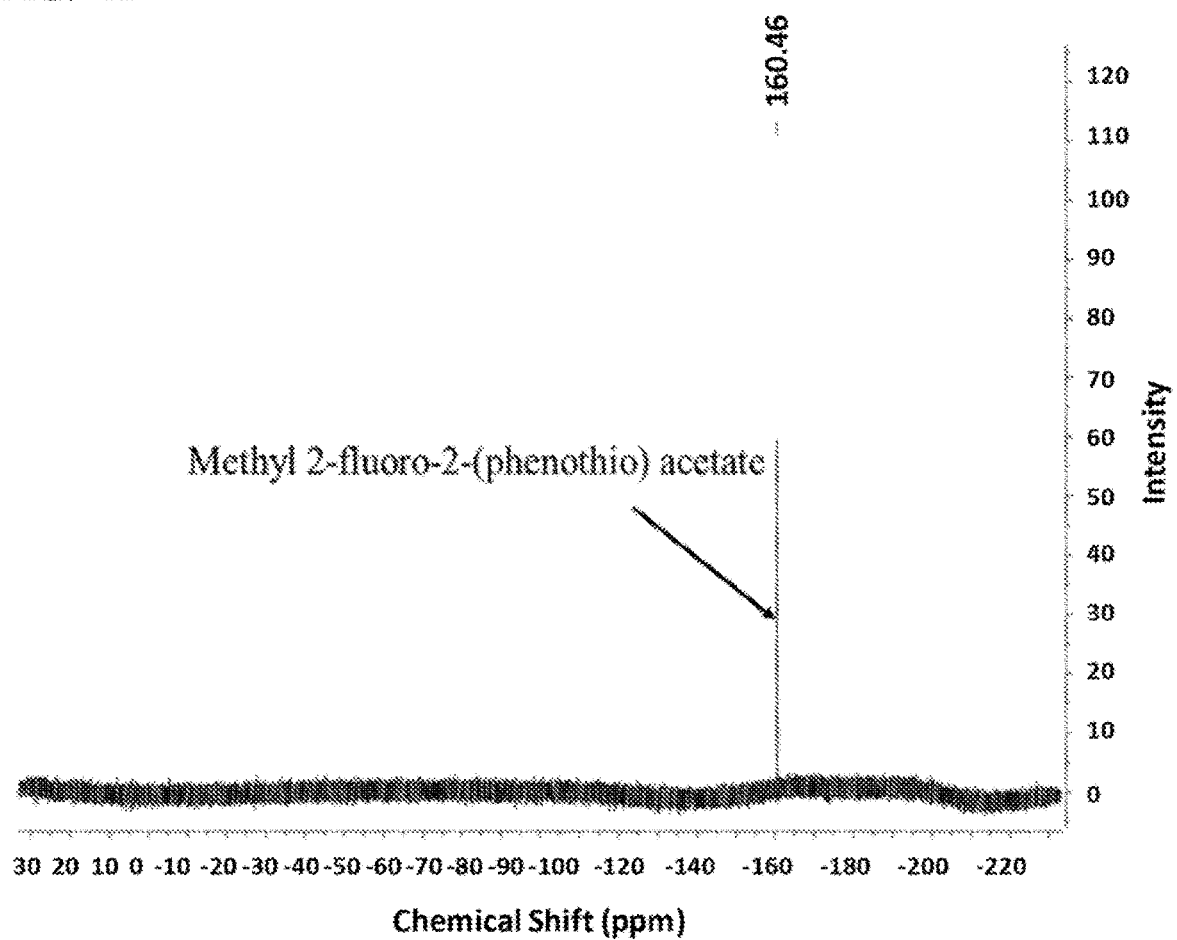
FIGS. 7A-7B.
Figure 7B:
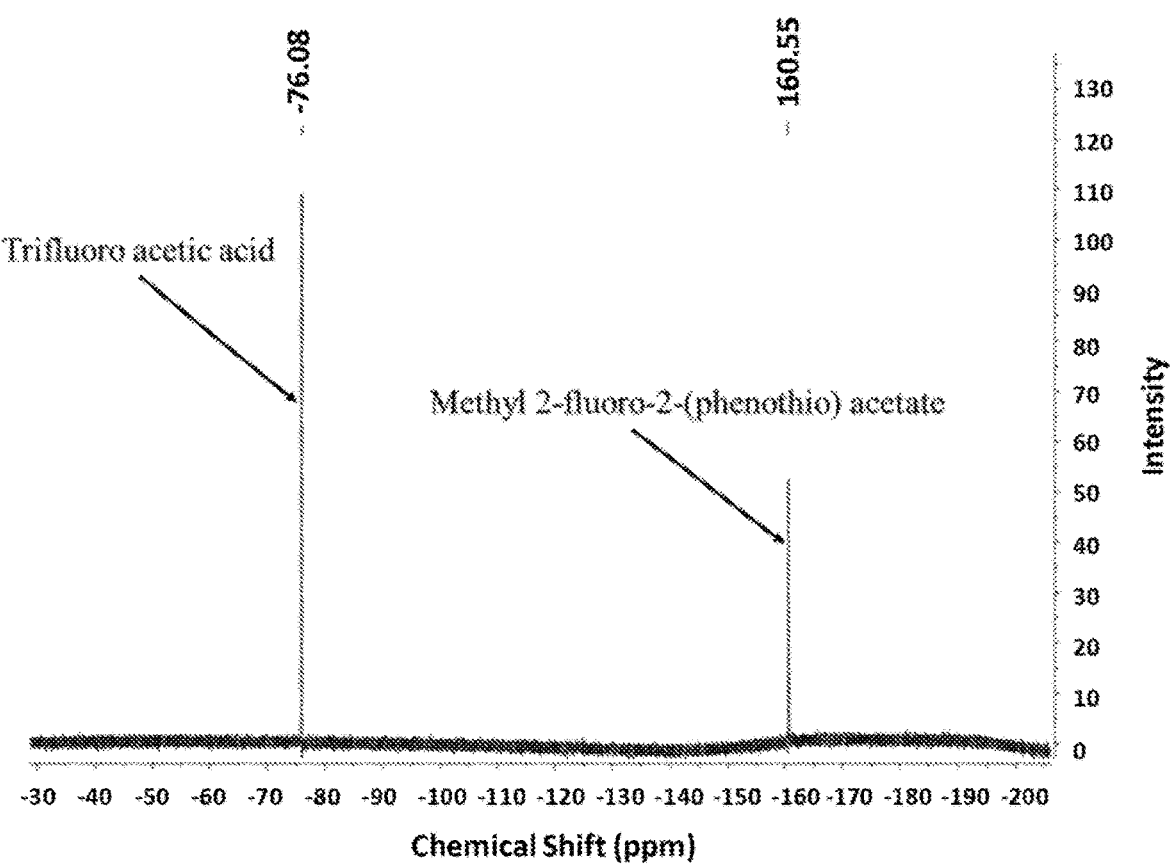

Nuclear magnetic resonance spectroscopy (NMR). The identity of the product 2 was also further characterized by $^{19}$F-NMR. The $^{19}$F-NMR spectrum was obtained on a Bruker AV400 (400 MHz). $^{19}$F chemical shift is reported in parts per million (ppm) using the trifluoro acetic acid ($CF_3COOH$) as a reference. FIG. 7 shows the $^{19}$F-NMR spectrum. $^{19}$F-NMR spectroscopic data for product 2 were in agreement with previous reports (Jouen et al, Tetrahedron, 1998, 54, 10801-10810).

Radiochemical characterization. No-carrier-added $^{18}$F-fluoride was produced by the (p,n) reaction of $^{18}O—H_2O$ (84% isotopic purity, Medical Isotopes) in a RDS-112 cyclotron (Siemens) at 11 MeV using a 1 mL tantalum target with havar foil. The radioactive isotope was trapped on analytical grade (AG) MP-1M anion exchange resin by passing through the 1 ml of bombarded $^{18}O—H_2O$. Most of the water on the resin was removed by washing with 10 mL of anhydrous ACN and drying with ultra-pure $N_2$ for 10 min. [$^{18}$F]fluoride was subsequently eluted out from the cartridge with a 2 ml TFE containing 25 mM TBAP salt. In a typical experiment, approximately 5 mCi was eluted from the anion exchange cartridge in $^{18}$F-TBAF form in TFE.

Radiofluorination conversion was measured using Radio-thin-layer-chromatography (radio-TLC). Radio-TLC was performed on silica plates (TLC Silica gel 60 W F254s, Merck). After dropping a sample volume (~1-5 μL) using a glass capillary, the plate was developed in the mobile phase (ACN). Chromatograms were obtained using a radio-TLC scanner (miniGita Star, Raytest). Analytical High Performance Liquid Chromatography (HPLC), equipped with a UV and gamma detector was used to determine radiochemical purity (RCP) of the radio-fluorinated product. HPLC was performed using a 1200 Series HPLC system (Agilent Technologies) equipped with a GabiStar flow-through gamma detector (Raytest). Data acquisition and processing was performed using GINA Star Software version 5.9 Service Pack 17 (Raytest). Typically, 20 μL of radioactive sample was diluted with 180 μL of ACN and 5-20 μL of this solution was injected for HPLC analysis. Column: Synergy 4u Polar RP 80 A, 250×4.6 mm, 4 micron. Gradient: A=ACN; B=water; flow rate=1.8 mL/min; 0-28 min 95% B to 45% B, 28-29 min 45% B to 5% B, 29-32 min 5% B, 32-34 min 5% B to 95% B. Radio-TLC chromatograms were used to measure radiochemical conversions (RCC). RCP and RCC were measured by dividing the area under the curve (AUC) for the desired product by the sum of AUC for all peaks. The TLC purity accounts for unreacted $^{18}$F-fluoride while the HPLC purity corrects for radiochemical side-products. The radiochemical fluorination efficiency (RCFE) was determined by the equation: RCFE=TLC RCC×HPLC RCP.

Figure 8A:
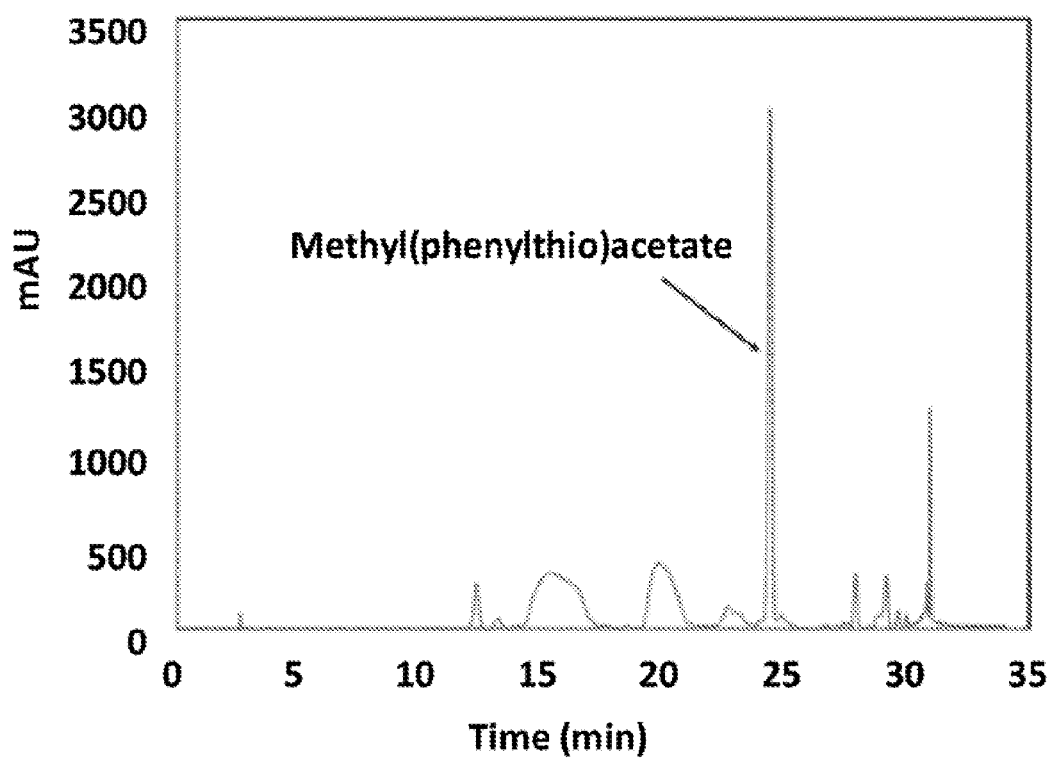
FIGS. 8A-8B show analytical profiles of the crude sample after electrolysis.
Figure 8B:
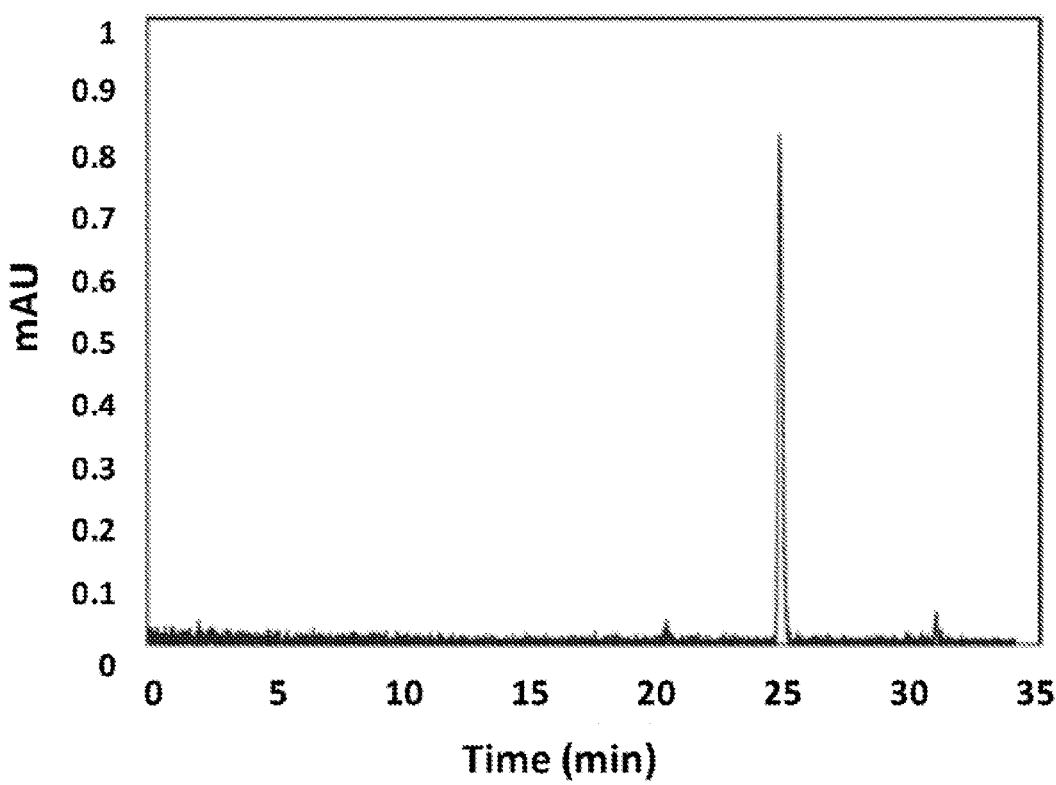
Figure 9:
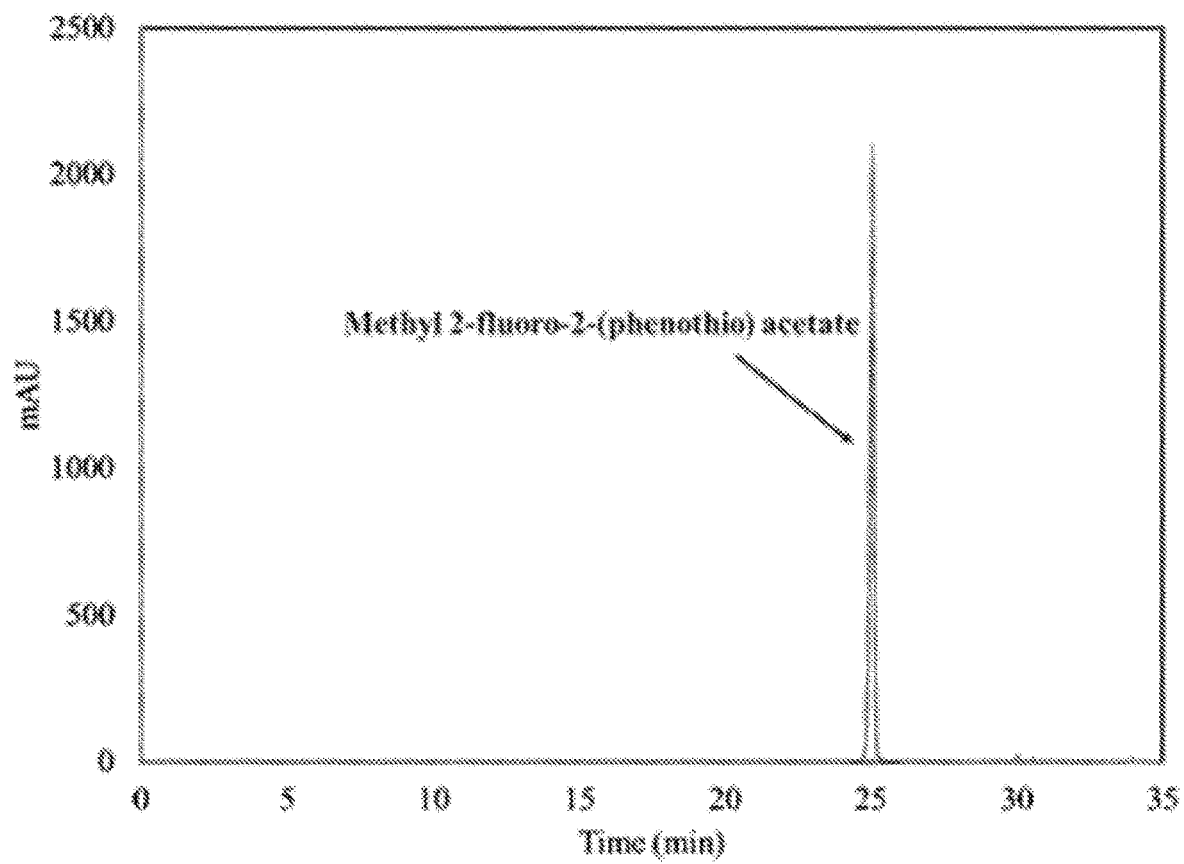
FIG. 9 shows UV HPLC profile of purified product. Electrolysis was performed for 60 min at 1.6 V vs Ag wire at −20° C. using TFE solution containing 24 mM of 1, 142 mM of triflic acid. 2 ml of TBAF solution was added after electrolysis was finished and the sample was HPLC purified 30 min after TBAF addition.
Figure 10:
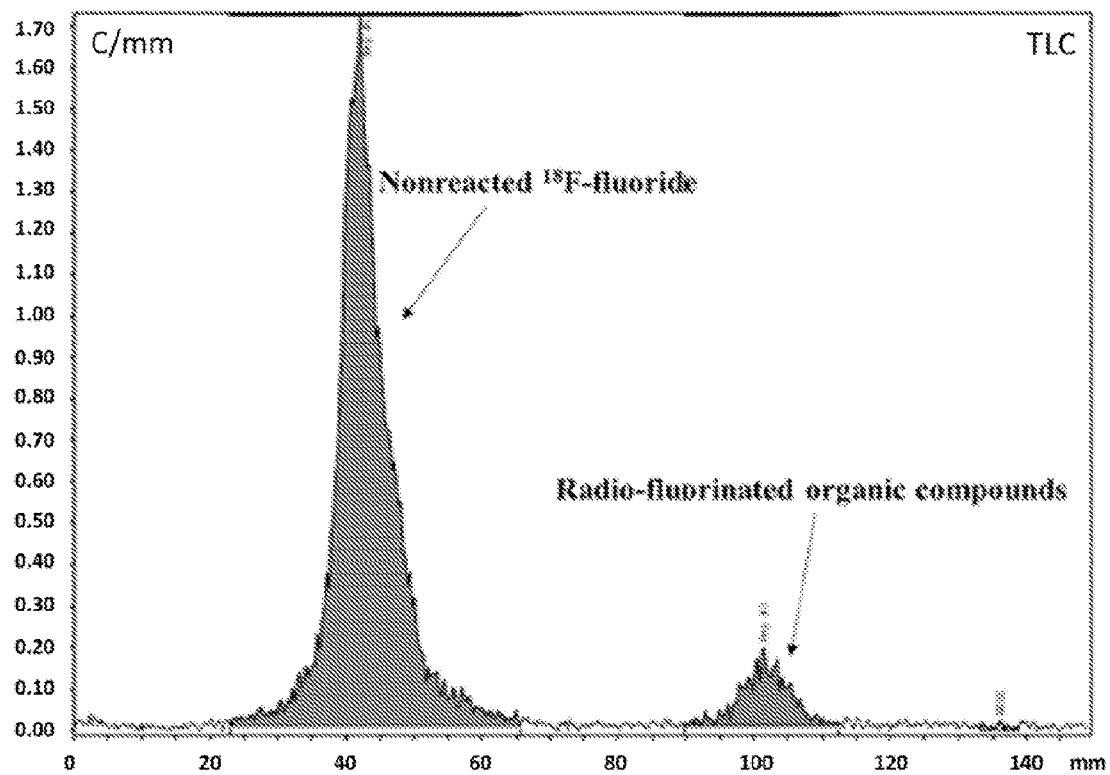
FIG. 10 shows gamma TLC of the crude sample post radio-electrochemical synthesis. Electrolysis was performed for 60 min at 1.6 V vs Ag wire at −20° C. using TFE solution containing 24 mM of 1, 142 mM of triflic acid. 2 ml of TFE solution containing 25 mM TBAP and 5 mCi 18F-fluoride was added after electrolysis was finished and the sample was taken for analysis 30 min after 18F-fluoride addition.

FIG. 8 shows the gamma+UV HPLC chromatograms of the crude product post radio-electrochemical synthesis. FIG. 9 shows UV HPLC chromatogram of HPLC purified product. FIG. 10 shows the gamma TLC trace of the crude product post radio-electrochemical synthesis.

Figure 11:
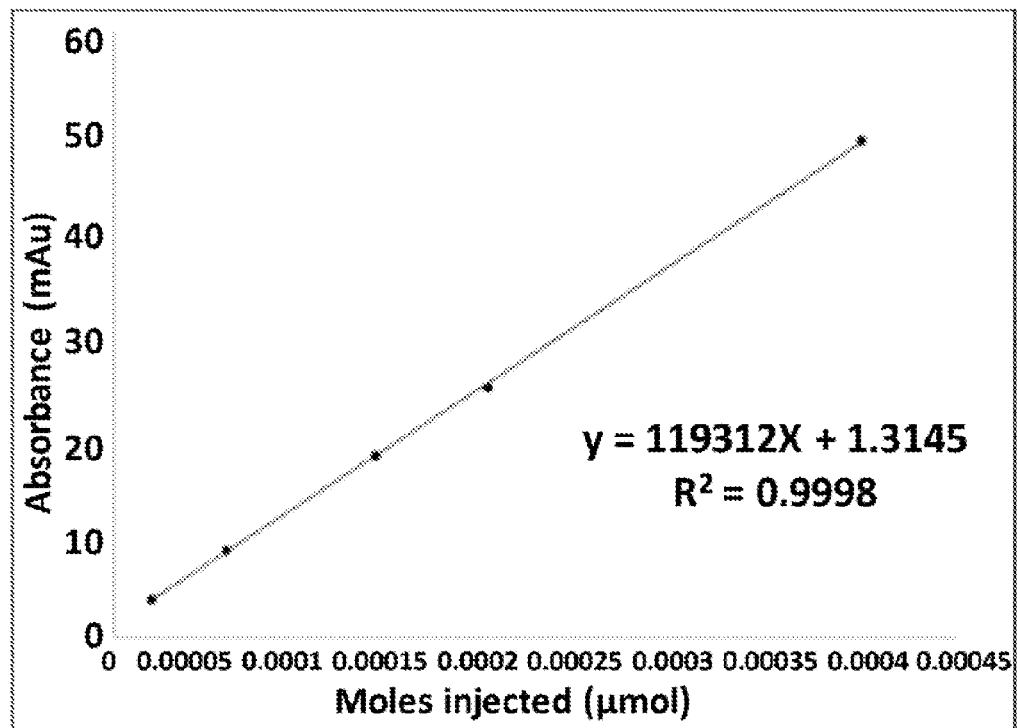
FIG. 11 shows the calibration curve of UV absorbance vs. molar mass.

Analytical HPLC was used to estimate molar activity ($A_m$) of [$^{18}$F]2. Calibration curve of UV absorbance vs. concentration (obtained at 254 nm) were created in advance for calculating $A_m$. $A_m$ was calculated by dividing the decay corrected radioactivity concentration by the molar concentration (as determined from the AUC for the UV peak and the calibration curve (FIG. 11)).

Example 2: Application of the Cation Pool Method for Fluorination and No-Carrier-Added Radio-Fluorination In 1999 Yoshida developed the cation pool method which stabilized carbamate cationic intermediates generated during a two electron oxidation followed by deprotonation that takes place in the anodic compartment of a two compartment cell under low temperatures (Yoshida, J. et. al. Direct Oxidative Carbon-Carbon Bond Formation Using the "Cation Pool" Method and Generation of Iminium Cation Pools and Their Reaction with Carbon Nucleophiles. J. Am. Chem. Soc. 121:9546-9549 (1999)). The method allows for rapid reactions with nucleophiles that may be unstable during electrolysis and can be added to the reaction mixture at the end of electrolysis to form the final product.

Here, we report on the extension of the cation pool method for the application of electrochemical fluorination and radio-fluorination of methyl (phenylthio)acetate. Electrochemical fluorination and no-carrier-added radiofluorination were successfully achieved using the cation pool method. The cation pool method has tremendous potential for radiofluorination experiments. The excess concentration of cations may provide an efficient reaction mechanism for late-stage fluorination under low fluoride concentrations encountered in radiochemistry. Furthermore, radiochemical yield, which is reduced by decay of the radioisotope, can benefit from a rapid late-stage fluorination reaction. The cation pool can be prepared prior to cyclotron production of 18F isotope, thereby, providing a rapid late-stage fluorination reaction, maximizing radiochemical yield by minimizing decay through a rapid reaction of the previously prepared cations with 18F-fluoride.

Synthesis parameters such as temperature, supporting electrolyte concentration and type, and precursor concentration were studied and optimized. The fluorination and radiofluorination yields of 12% and 6.7% were obtained, respectively, using the optimum conditions. The products were characterized using gas chromatography-mass spectrometry (GC-MS), nuclear magnetic resonance (NMR), radio-thin-layer chromatography (radio-TLC) and high-performance liquid chromatography (HPLC). This method can also be applied for a late-stage no-carrier-added radiofluorination to develop new positron emission tomography (PET) tracers.

The section headings used herein are for organizational purposes only and are not to be construed as limiting the subject matter described. All documents, or portions of documents, cited in the application including, are incorporated by reference in their entirety for any purpose.

While various embodiments and aspects are shown and described herein, it will be obvious to those skilled in the art that such embodiments and aspects are provided by way of example only. Numerous variations, changes, and substitutions will now occur to those skilled in the art. It should be understood that various alternatives to the embodiments described herein may be employ.

What is claimed is:

1. A method of producing an $^{18}$F fluorinated organic compound, the method comprising the steps of:
   (i) performing electrochemical oxidation on a plurality of organic compounds, thereby forming a plurality of carbocations; and
   (ii) subsequently adding a plurality of fluorinated nucleophiles to the plurality of carbocations, wherein the plurality of fluorinated nucleophiles comprises $^{18}$F-fluorinated nucleophiles and $^{19}$F-fluorinated nucleophiles, and wherein the plurality of carbocations is in molar excess relative to the plurality of fluorinated nucleophiles, thereby forming the $^{18}$F fluorinated organic compound; wherein performing electrochemical oxidation comprises performing electrochemical oxidation in a liquid medium which comprises a mixture comprising:
   (a) the plurality of organic compounds and an organic solvent;
   (b) the plurality of organic compounds, an organic solvent, and an acid;
   (c) the plurality of organic compounds, an organic solvent, and a base;
   (d) the plurality of organic compounds, an acid, and a base; or
   (e) the plurality of organic compounds, an organic solvent, an acid, and a base; and wherein the plurality of organic compounds, the acid and the base are present in an amount effective to stabilize the plurality of carbocations.

2. The method of claim 1, wherein the method comprises performing electrochemical oxidation at a reduced temperature, and wherein the reduced temperature is less than 0° C.

3. The method of claim 1, wherein performing electrochemical oxidation comprises performing electrochemical oxidation in the liquid medium which comprises the mixture comprising the plurality of organic compounds, the organic solvent, and the acid.

4. The method of claim 3, wherein the molar ratio of the organic solvent to the acid is from about 0.8:1 to about 3:1.

5. The method of claim 1, wherein:
   (i) the organic solvent is trifluoroethanol, hexafluoroisopropanol, or a combination thereof;
   (ii) the acid is trifluoromethanesulfonic acid, tetrabutylammonium perchlorate, tetrabutylammonium tetrafluoroborate, trifluoroacetic acid, p-toluenesulfonic acid, or a combination thereof; and
   (iii) the base is a conjugate base of trifluoromethanesulfonic acid, a conjugate base of tetrabutylammonium perchlorate, a conjugate base of tetrabutylammonium tetrafluoroborate, trifluoroacetic acid, a conjugate base of p-toluenesulfonic acid, or a combination thereof.

6. The method of claim 5, wherein: (i) the acid is trifluoromethanesulfonic acid and the base is the conjugate base of trifluoromethanesulfonic acid; (ii) the acid is tetrabutylammonium perchlorate and the base is the conjugate base of tetrabutylammonium perchlorate; (iii) the acid is tetrabutylammonium tetrafluoroborate and the base is the conjugate base of tetrabutylammonium tetrafluoroborate; (iv) the acid is trifluoroacetic acid and the base is the conjugate base of trifluoroacetic acid; or (v) the acid is p-toluenesulfonic acid and the base is the conjugate base of p-toluenesulfonic acid.

7. The method of claim 1, wherein adding the plurality of fluorinated nucleophiles to the plurality of carbocations comprises adding the plurality of fluorinated nucleophiles to the mixture of (a), (b), (c), (d), or (e).

8. The method of claim 1, wherein each of the plurality of organic compounds comprises a saturated carbon atom.

9. The method of claim 1, wherein each of the plurality of carbocations forms part of a substituted or unsubstituted aromatic or heteroaromatic ring when in neutral form or is adjacent to a carbonyl moiety, an amide moiety, an ester moiety, a sulfur atom, or a thioether moiety.

10. The method of claim 1, wherein the plurality of fluorinated nucleophiles comprises $K(^{18}F)F$—K222, cesium fluoride, potassium fluoride, triethylamine trihydrofluoride, or tetrabutylammonium fluoride.

11. The method of claim 1, wherein the plurality of fluorinated nucleophiles is a no-carrier added plurality of fluorinated nucleophiles.

* * * * *